United States Patent
Bene

(10) Patent No.: US 8,246,567 B2
(45) Date of Patent: Aug. 21, 2012

(54) METHOD OF MONITORING HYPERTENSIVE HAEMODIALYSIS PATIENTS

(75) Inventor: Bernard Bene, Irigny (FR)

(73) Assignee: Gambro Lundia AB, Lund (SE)

( * ) Notice: Subject to any disclaimer, the term of this patent is extended or adjusted under 35 U.S.C. 154(b) by 420 days.

(21) Appl. No.: 12/523,460

(22) PCT Filed: Jan. 16, 2008

(86) PCT No.: PCT/IB2008/000089
§ 371 (c)(1),
(2), (4) Date: Dec. 21, 2009

(87) PCT Pub. No.: WO2008/087528
PCT Pub. Date: Jul. 24, 2008

(65) Prior Publication Data
US 2010/0105990 A1    Apr. 29, 2010

(30) Foreign Application Priority Data

Jan. 17, 2007 (FR) ..................... 07 00298

(51) Int. Cl.
*A61M 37/00* (2006.01)
*C02F 1/44* (2006.01)

(52) U.S. Cl. ..................... 604/5.04; 604/6.01; 604/6.09; 210/645; 210/739

(58) Field of Classification Search ................. 604/4.01, 604/5.01, 5.04, 6.01, 6.09; 210/645, 646, 210/739
See application file for complete search history.

(56) References Cited

U.S. PATENT DOCUMENTS
| | | | |
|---|---|---|---|
| 6,110,384 A | 8/2000 | Goux et al. | |
| 2004/0225201 A1 | 11/2004 | McNair | |
| 2005/0228241 A1 | 10/2005 | McNair | |

FOREIGN PATENT DOCUMENTS
| | | |
|---|---|---|
| EP | 0 547 025 B1 | 6/1993 |
| EP | 0 920 877 B1 | 6/1999 |
| WO | 2006/031186 A1 | 3/2006 |
| WO | 2008/087470 A1 | 7/2008 |

OTHER PUBLICATIONS

Gotch Frank A. and Sargent John A., "A mechanistic analysis of the National Cooperative Dialysis Study (NCDS)", Kidney International, vol. 28 (1985), pp. 526-534.
Henrich, M.D. William L., "Principles and Practice of Dialysis", Second Edition, Lippincott Williams & Wilkins, Philadelphia, PA, published at least as early as Jan. 16, 2008, pp. 216-217.
Purcell Wendy et al., "Accurate Dry Weight Assessment: Reducing the Incidence of Hypertension and Cardiac Disease in Patients on Hemodialysis", Nephrology Nursing Journal, Nov.-Dec. 2004, vol. 31, No. 6, pp. 631-638.
Chazot C. and Charra B., "Non pharmacologic treatment of hypertension in hemodialysis patients", Néphrologie & Thérapeutique, Hypertension et dialyse, ISSN 1769-7255, Oct. 2007, vol. 3, Supplement 3, pp. 5178-5184. English Abstract.

*Primary Examiner* — Leslie Deak
(74) *Attorney, Agent, or Firm* — Pearne & Gordon LLP

(57) ABSTRACT

The invention relates to a calculation and control system for determining whether a patient intended to follow several sessions of hemodialysis treatment falls or not within one group among several groups of hypertension-affected patients, the system comprising:
a) means for determining the value of at least one parameter representing the mass interdialytic evolution of the patient, for at least two sessions,
b) means for determining the value of at least one parameter representing the plasmatic conductivity of the patient for at least two sessions,
c) means for determining the value of a parameter representing the ionic mass transfer of the treatment for at least two sessions,
d) programmed means for determining whether the patient falls or not within a group of hypertension-affected patients as a function of the interdialytic mass evolution of the patient, and/or of the plasmatic conductivity and/or of the ionic mass transfer.

39 Claims, 13 Drawing Sheets

METHOD OF MONITORING HYPERTENSIVE HAEMODIALYSIS PATIENTS

TECHNICAL FIELD OF THE INVENTION

The present invention relates to the determination whether a patient subjected to successive sessions of extracorporeal blood treatment falls or not within a group of hypertension-affected patients, and in particular relates to a method and to new, improved devices for determining whether a patient subjected to successive sessions of extracorporeal blood treatment falls or not within a group of hypertension-affected patients, and for proposing or urging the change of some parameters so as to make up for some unwanted effects of detected hypertension.

STATE OF THE PRIOR ART

Extracorporeal blood treatment is used with patients incapable of effectively eliminating materials from their blood, for example in the case of a patient who suffers from a temporary or permanent failure of the kidneys. These patients and other patients can follow an extracorporeal treatment of the blood to add or eliminate materials in their blood, to maintain an acid-base balance or to eliminate excess body fluids, for example.

Extracorporeal treatment of the blood is typically performed by drawing the patient's blood in a continuous stream, introducing the blood into a primary chamber of a treatment unit (or filter) in which the blood passes across a semi-permeable membrane.

The circuit comprising a needle for drawing the blood via the patient's vascular access, a bleed-off line or arterial line, the first compartment of the treatment unit, a return line or venous line and a needle for returning the blood by injecting it via the vascular access, is called an extracorporeal blood circuit.

The semi-permeable membrane allows, in a selective manner, undesirable materials contained in the blood to pass across the membrane, from the primary chamber to the secondary chamber, and also allows, in a selective manner, beneficial materials contained in the liquid entering the secondary chamber to pass across the membrane to the blood entering the primary chamber, as a function of the type of treatment.

There are several types of extracorporeal blood treatments. Such treatments comprise, for example, hemodialysis, hemofiltration, hemodiafiltration, plasmapheresis, blood oxygenation, etc.

A patient may suffer from a permanent failure of the kidneys. In this case, he will have to undergo regular sessions, for example three times a week, of extracorporeal blood treatment with a relatively high blood extraction flowrate, namely roughly between 150 and 500 ml/min. The approximate duration of these sessions is from three to four hours.

It is known that patients undergoing a chronic dialysis treatment may suffer from hypertension. Hypertension is a major cause of heart-related death for patients undergoing a chronic dialysis treatment.

It is known about a first scientific publication entitled "Principles and Practice of Dialysis, Second Edition", in which the author William L. Einrich recommends some basic principles concerning the lifestyle of hypertension-affected dialyzed patients. Among these, reducing sodium assumption, intensifying physical exercise, limiting daily assumption of alcoholic drinks, avoiding smoking, eliminating the use of cocaine or amphetamines.

Moreover, it is known about a second scientific publication entitled "Néphrologie et thérapeutique—hypertension et dialyse" of October 2007, volume 3 annex 3, in which the authors CChazot and B. Charra deal with non-medical treatments of arterial hypertension in hemodialysis. This publication states that "the correction of arterial hypertension in hemodialysis takes place by means of the dry weight method, which includes a progressive reduction of the dialysis final weight until arterial pressure is normalized. Related necessary measures are a salt-free diet and the maintenance of sodium balance during the session, the stop of hypertension factors, a sufficient duration of the dialysis session and the pedagogical effort towards the patient." However, these parameters are quoted as an illustrative list, without differentiating one from the other and without assigning a priority thereto.

Finally, it is known about a third publication in the magazine "Nephrology nursing" of November-December 2004, vol. 31, number 6, by Wendy Purcell, Elisabeth Manias, Allison Williams and Rowan Walker. According to this article, the elimination of excess water in the patient during the hemodialysis session can successfully normalize arterial pressure, provided that the desired dry weight is exactly reached at the end of the session.

Nonetheless, the Applicant does not know about any system enabling today to successfully and automatically determine whether a patient falls or not within a group of hypertension-affect patients subjected to sessions of extracorporeal blood treatment, or to recommend the change of a specific parameter so as to try to make up for this detected group.

It is therefore necessary to obviate to this lack by means of a method and a device for successfully determine the hypertension status of the patient, enabling an improved monitoring of unwanted hypertension and a faster, downstream identification of the drawbacks relating to such hypertension.

ACCOUNT OF THE INVENTION

The invention relates to a calculation and control system for determining whether a patient intended to follow several sessions (i, j) of extracorporeal blood treatment by extraction and return of the blood via the vascular access, falls or not within a group among several groups of hypertension-affected patients, the system comprising the following means:
 a) means for determining the value of at least one parameter ($\Delta Pi$, $\Delta Pj$ . . . ) representing the evolution of the interdialytic mass ($\Delta P$) of the patient, for at least two sessions (i, j . . . ),
 b) means for determining the value (CPi, CPj, . . . ) of at least one parameter representing the plasmatic conductivity (CP) of the patient for at least two sessions (i, j),
 c) means for determining the value (TMi, TMj) of a parameter representing the ionic mass transfer of the treatment for at least two sessions (i, j),
 d) programmed means for determining whether the patient falls or not within a group of hypertension-affected patients as a function of the evolution over several sessions of at least one of the three following sets of values:
  a first set of at least two determined values ($\Delta Pi$, $\Delta Pj$) of the evolution of the interdialytic mass ($\Delta P$) of the patient,
  a second set of at least two determined values (CPi, CPj . . . ) representing the plasmatic conductivity; and
  a third set of at least two determined values (TMi, TMj) representing the ionic mass transfer.

The invention also relates to a computer comprising:
storage means storing at least values of at least one parameter (Pi, Pj . . . ) representing the mass (P) of the patient, at least values of at least one parameter (CPi, CPj . . . ) representing the patient's plasmatic conductivity, and values of at least one parameter representing the ionic mass transfer (TMi, TMj . . . ) relating to at least one patient undergoing several sessions (i, . . . j) of extracorporeal blood treatment,
a calculation and control system according to the invention for determining whether the patient whose parametric values of at least one parameter (Pi, Pj . . . ) representing the mass (P) of the patient, whose values of at least one parameter representing the plasmatic conductivity (CP) and whose values of at least one parameter representing the ionic mass transfer are stored in said storage means, falls or not within a group of hypertension-affected patients.

The invention also relates to an extracorporeal blood treatment machine comprising at least:
a blood treatment unit capable of implementing an extracorporeal blood treatment by blood circulation via an extracorporeal blood circuit comprising an arterial line, a first chamber of a filter separated by a semi-permeable membrane, a venous line, and by dialysate circulation in a second chamber of the filter,
storage means storing at least values of at least one parameter (Pi, Pj . . . ) representing the miss (P) of the patient, at least values of at least one parameter (CPi, CPj . . . ) representing the patient's plasmatic conductivity, and values of at least one parameter representing the ionic mass transfer (TMi, TMj . . . ) relating to at least one patient undergoing several sessions (i, . . . j) of extracorporeal blood treatment,
a calculation and control system according to the invention for determining whether the patient whose parametric values of at least one parameter (Pi, Pj . . . ) representing the mass (P) of the patient, whose values of at least one parameter (CPi, representing the patient's plasmatic conductivity and whose values of at least one parameter representing the ionic mass transfer (TMi, TMj . . . ) are stored in said storage means, falls or not within a group of hypertension-affected patients.

The invention further relates to a network comprising:
a server,
at least one blood treatment machine linked to the server, each machine comprising:
means for measuring and/or for calculating medical data relating at least one parameter (Pi, Pj . . . ) representing the mass of the patient, at least one parameter (CPi, CPj . . . ) representing the patient's plasmatic conductivity and at least one parameter representing the ionic mass transfer (TMi, TMj . . . ),
means for sending at least part of these measured and/or calculated data to the server,
the server comprising:
means for receiving at least part of the medical data relating to extracorporeal blood treatments,
storage means for storing the data received from the reception means from one or more blood treatment machines,
a calculation and control system according to the invention, intended to operate on the basis of said received data,
at least one station capable of communicating with the server for receiving at least the results of the implementation of said calculation and control system.

The invention also relates to a method for determining whether a patient intended to follow successive sessions (i, j) of extracorporeal blood treatment by extraction and return of the blood falls or not within a group of hypertension-affected patients, the method of determination comprising the following steps:
a) determining the value of at least one parameter (Pi, Pj . . . ) representing the mass (P) of the patient for at least two sessions (i, j . . . ),
b) determining the value (CPi, CPj, . . . ) of at least one parameter representing the patient's plasmatic conductivity (CP) for at least two sessions(i, j),
c) determining the value (TMi, TMj) of at least one parameter representing the ionic mass transfer of the treatment for at least two sessions (i, j),
d) determining whether the patient falls or not within a group of hypertension-affected patients as a function of the evolution over several sessions of at least one of the three following sets of values:
a first set of at least two determined values (Pi, Pj) representing the patient's mass,
a second set of at least two determined values (CPi, CPj . . . ) representing the plasmatic conductivity; and
a third set of at least two determined values (TMi, TMj) representing the ionic mass transfer.

Finally, the invention eventually relates to a computer program for determining whether a patient falls or not within a group of hypertension-affected patients, which program is loadable into the internal memory of a computer, comprising portions of computer program code for, when the program is executed by the computer, implementing the method according to the invention.

BRIEF DESCRIPTION OF THE DRAWINGS

We shall refer to the appended drawings in FIGS. 1 to 19 in which.

DETAILED ACCOUNT OF THE INVENTION

Figure 1:
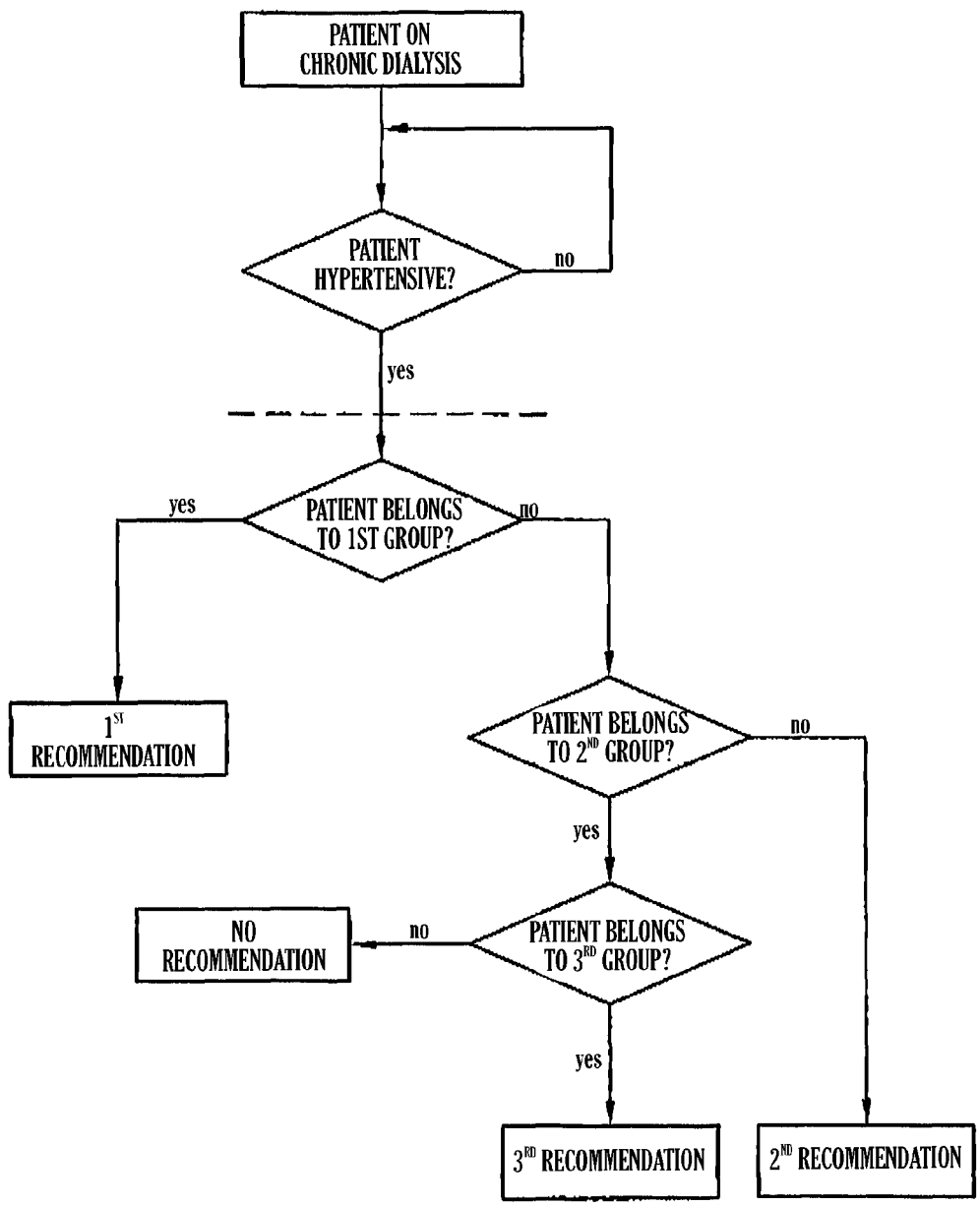
FIGS. 1 and 2 represent the general and specific steps, respectively, of the method for determining whether a patient falls or not within a group of hypertension-affected patients.

A calculation and control system for determining whether a patient intended to follow several sessions (i, j) of extracorporeal blood treatment by extraction and return of the blood via the vascular access, falls or not within a group of hypertension-affected patients, the system comprising the following means:

a) means for determining the value of at least one parameter (ΔPi, ΔPj . . . ) representing the evolution of the interdialytic mass (ΔP) of the patient, for at least two sessions (i, j. . . ), b) means for determining the value (CPi, CPj, . . .) of at least one parameter representing the plasmatic conductivity (CP) of the patient for at least two sessions (i, j), c) means for determining the value (TMi, TMj) of a parameter representing the ionic mass transfer of the treatment for at least two sessions (i, j), d) programmed means for determining whether the patient falls or not within a group of hypertension-affected patients as a function of the evolution over several sessions of at least one of the three following sets of values:

a first set of at least two determined values (ΔPi, ΔPj) of the evolution of the interdialytic mass (ΔP) of the patient, a second set of at least two determined values (CPi, CPj . . . ) representing the plasmatic conductivity; and a third set of at least two determined values (TMi, TMj) representing the ionic mass transfer.

For the whole invention, the calculation and control system can take the form of a duly programmed analog or duly programmed digital calculation and control unit, comprising at least one microprocessor and at least one duly programmed memory. The memories may be one from among or a combination of the following memories: magnetic memory, RAM memory, ROM memory, or any other memory envisageable by the person skilled in the art.

The means for determining the value of at least one parameter representing the evolution of the interdialytic mass of the patient, the means for determining the value of parameters representing the plasmatic conductivity, and the means for determining the value of parameters representing the ionic mass transfer and the purification effectiveness can consist of:

a) at least one memory containing the value of these parameters, which memory the programmed means will be able to consult to ascertain the chosen values, and/or b) apparatus for detecting the corresponding parameters:
weight or mass detectors or sensors such as spring balances, scales . . . ,
means for measuring the conductivity or concentration of a substance in blood, e.g. means for detecting the plasmatic conductivity for sodium, which are known for instance under the name DIASCAN sold by GAMBRO and to which reference is made in the detailed description of patent EP 0 547 025, implemented by sensors, biosensors, microsensors,
means for measuring the ionic mass transfer, which can be calculated for instance as follows:
TMI=Q2*C2−Q1*C1, wherein Q1 and Q2 are the ionic flowrates of the dialysate getting in and out of the dialyzer, respectively, and C1 and C2 are the ion concentrations getting in and out of the dialyzer, respectively, the flowrate and concentration of sodium ion representing the whole set can be taken into account, c) a calculation and control unit which will be duly programmed to implement the method according to the invention.

Moreover, the system according to the invention is capable of determining the hypertension groups divided into a first group of hypertension-affected patients, a second group of hypertension-affected patients, and a third group of hypertension-affected patients. As a matter of fact, the point is to divide the population of hypertension-affected patients into several groups according to the historical evolution over several sessions of some of their parameters. The invention can include two or three groups.

The system according to the invention has programmed means for determining whether the patient falls or not within a group of hypertension-affected patients, comprising programmed means for determining whether the patient falls or not within the first group.

The system according to the invention has programmed means for determining whether the patient falls or not within a group of hypertension-affected patients, comprising programmed means for determining whether the patient falls or not within the second group when the patient does not fall within the first group.

The system according to the invention has programmed means for determining whether the patient falls or not within a group of hypertension-affected patients, comprising programmed means for determining whether the patient falls or not within the third group when the patient does not fall within the second group.

In the system according to the invention, the value (ΔPi, ΔPj . . . ) representing the interdialytic evolution of the mass (ΔP) of the patient, for at least two sessions (i, j . . . ), is chosen from the group comprising:

the weight increase of the patient between the end of one session (i) and the beginning of the following session (i+1)), the mass increase of the patient between the end of one session (i) and the beginning of the following session (i+1), a parameter proportional to one of the aforesaid parameters.

In the system according to the invention, the parameter representing the plasmatic conductivity is the same as or function of at least one of the following parameters:

the plasmatic conductivity of the patient, the predialytic plasmatic conductivity of the patient, i.e. the plasmatic conductivity before the session of extracorporeal blood treatment, a parameter proportional to one of the aforesaid parameters.

In the system according to the invention, the extracorporeal parameter or parameters have been measured for one session of extracorporeal blood treatment, which consists in circulating the patient's blood at an extracorporeal blood flowrate and in an extracorporeal blood circuit, this circuit comprising an arterial line where there exists an arterial pressure, a filter and a venous line where there exists a venous pressure. Moreover, the filtrate or dialysate circuit consists in extracting from the filter a filtrate by means of a drain line or in contacting dialysate with blood in the filter separated by a semi-permeable membrane in the dialysate circuit, comprising an intake line for dialysate to the filter and a drain line for used dialysate from the filter. The plasmatic conductivity is the conductivity of the patient's plasma.

In the system according to the invention, the parameter representing the ionic mass transfer for at least two sessions (i, j) is the same as or function of at least one of the following parameters:

the ionic mass transfer during the session, the sodium mass transfer during the patient's session, a parameter proportional the one of the aforesaid parameters.

The values of the parameter or parameters representing the ionic mass transfer can be average values of this parameter over a treatment session. These values can either be an instantaneous value chosen at a time t of the session, at the beginning, in the middle or at the end of the session, or can further be a mean value, or any other mathematical value representing as accurately as possible the parameter or the evolution thereof over a dialysis session.

The values of the parameter or parameters representing the plasmatic conductivity can be for instance values of plasmatic conductivity before the session, more specifically at the beginning of the treatment session.

It will be obvious that the implementation of the method according to the invention is clearly divided from the extracorporeal blood treatment.

The system according to the invention can include means for determining the patient's pressure. This pressure can be arterial pressure (preferably), systolic pressure, the average between arterial pressure and systolic pressure. This pressure can be measured with the patient lying down, before the beginning of the session.

In the system according to the invention, the patient is initially considered as hypertension-affected when the values representing his/her pressure increase of at least about 20 mmHg over at least two sessions and/or the value of his/her pressure for one session is above about 150 mmHg or above 150 mmHg. Preferably, the initial status of hypertension-affected patient can further be confirmed when, additionally, the increase in the values representing his/her pressure remains stable over the considered temporal lapse. In order to verify if pressure evolution remains stable, known mathematical methods can be used, such as for instance the least square method. This applies to the evolution of all representative values according to the invention.

Figure 3:
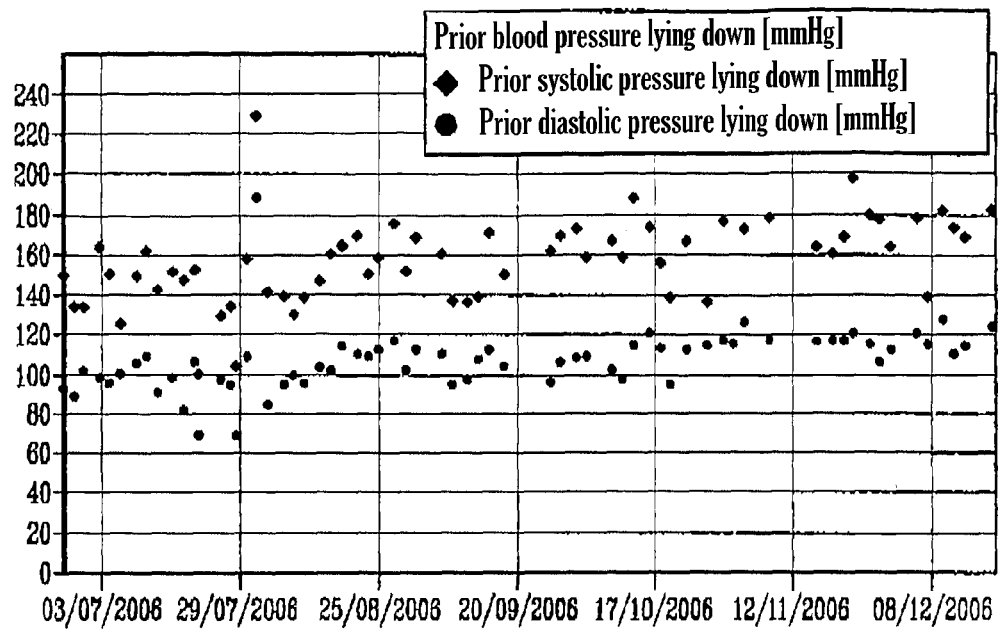
FIGS. 3, 4 and 5 represent examples of variation of a patient's pressure with different variables of a patient.
Figure 4:
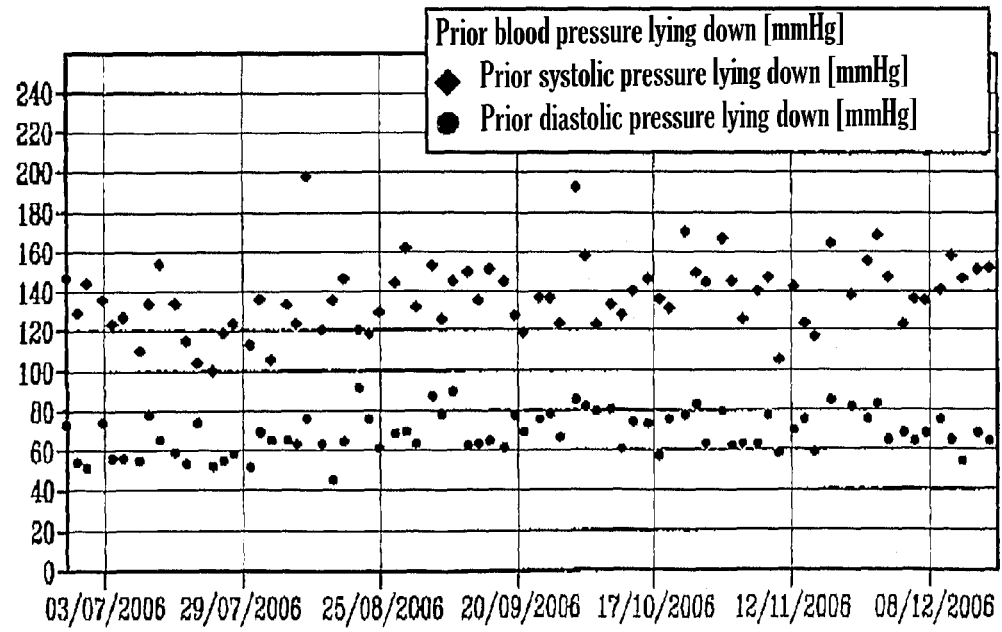
Figure 5:
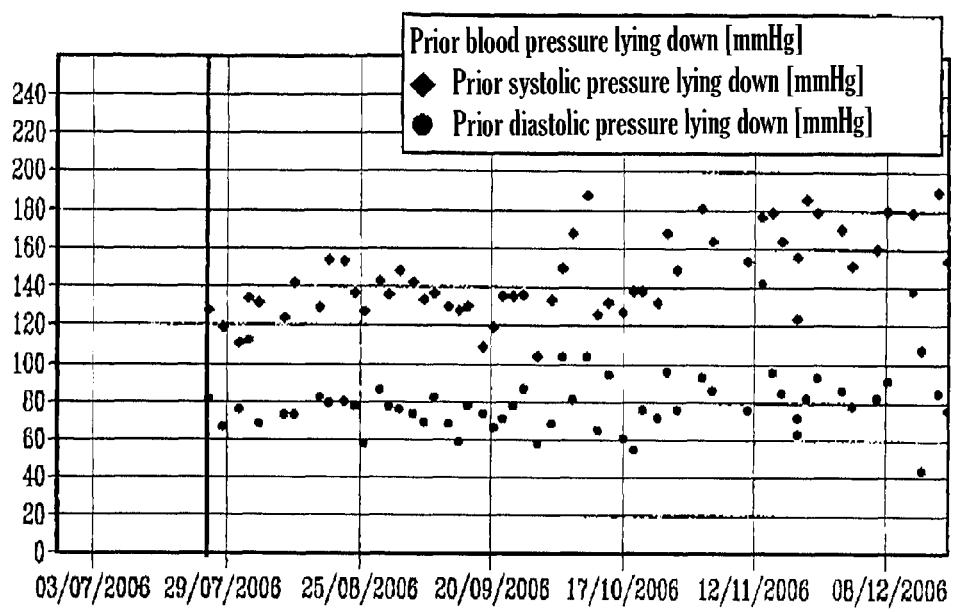
Figure 6:
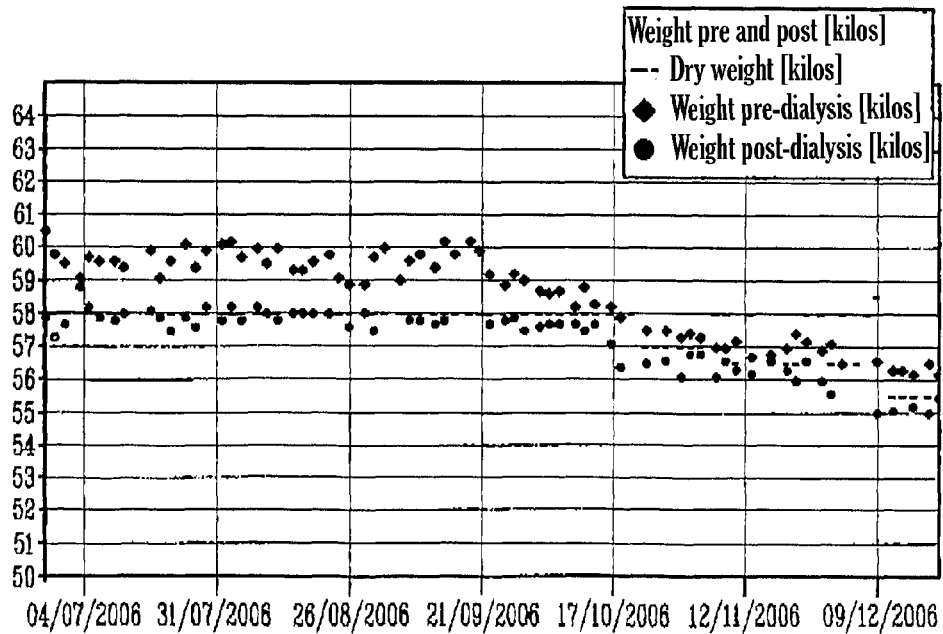
FIGS. 6 and 7 represent examples of variation of the interdialytic weight increase and of variation of a patient's dry weight.
Figure 7:
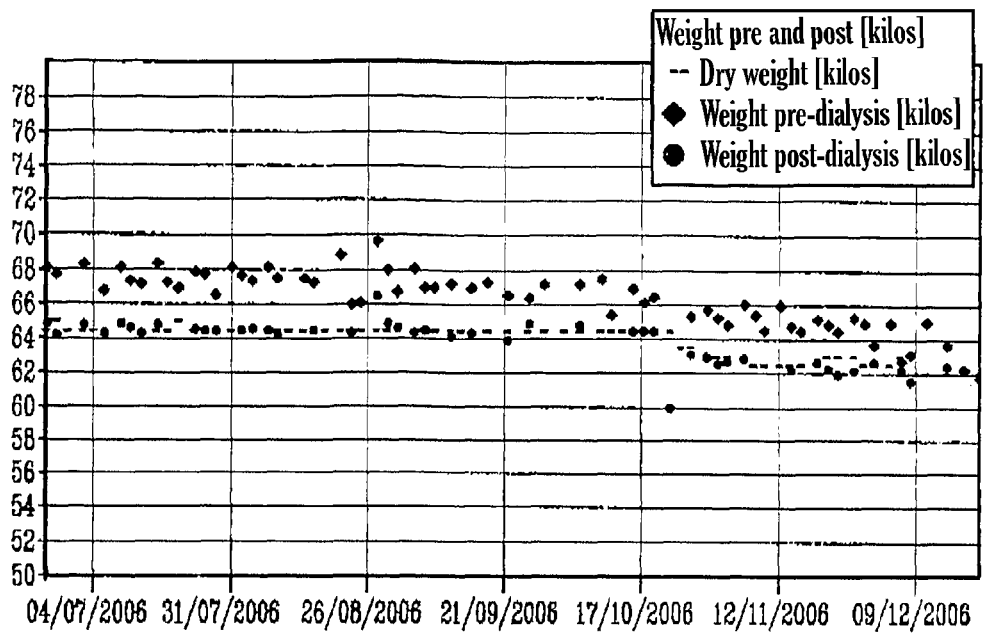
Figure 8:
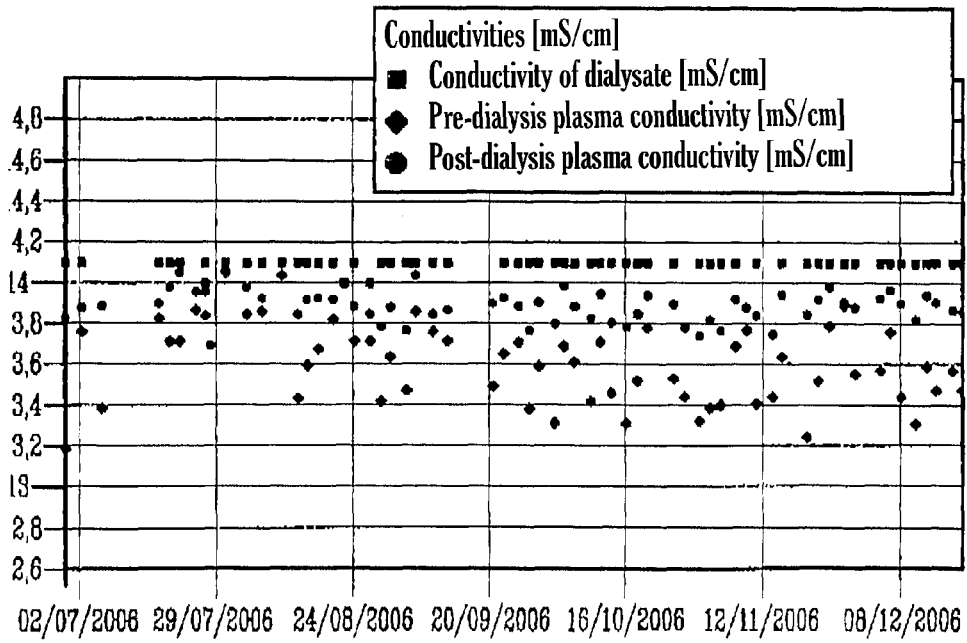
FIGS. 8, 9, 10 and 11 represent examples of variation over several months of the predialytic plasmatic conductivity of a patient.
Figure 9:
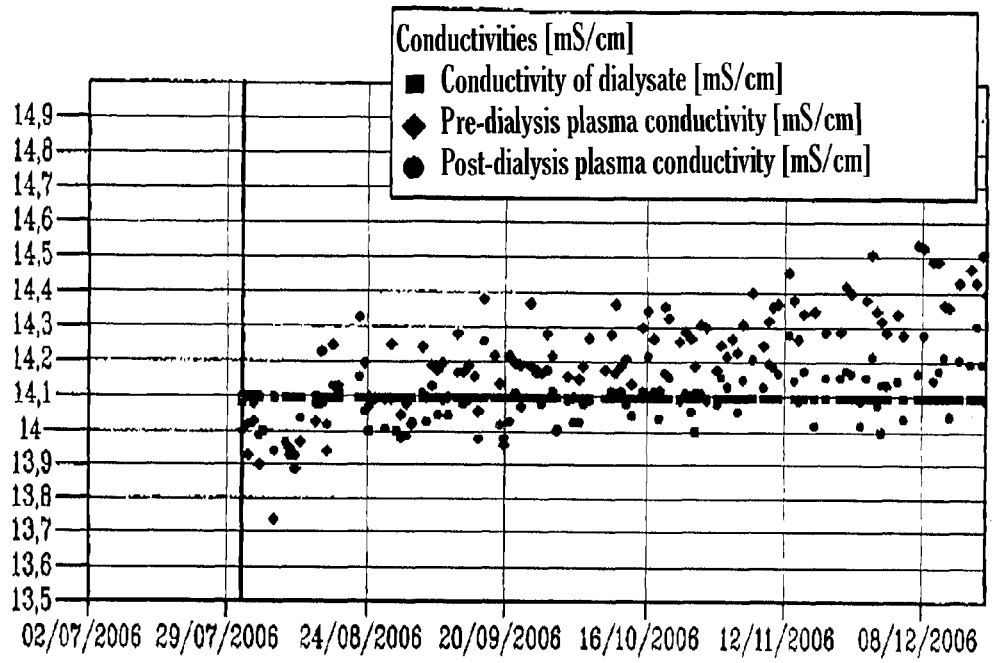
Figure 10:
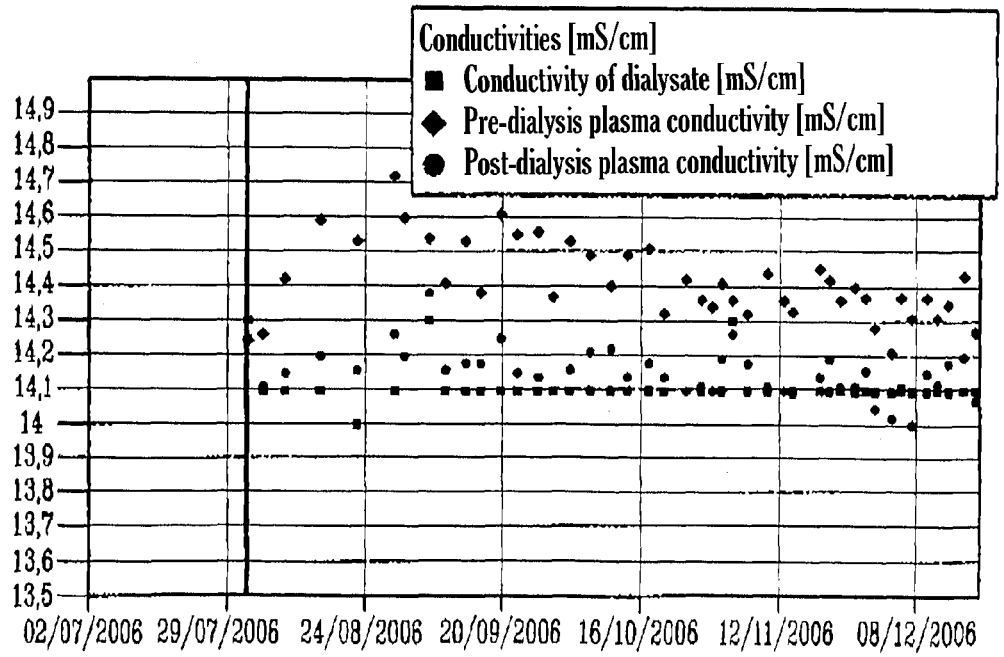
Figure 11:
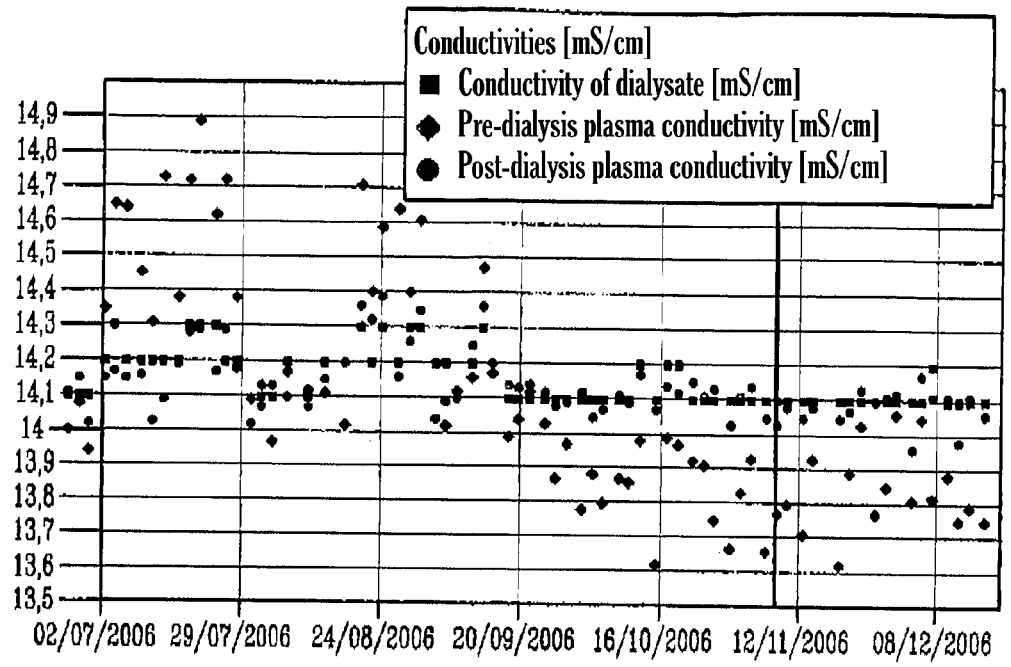
Figure 12:
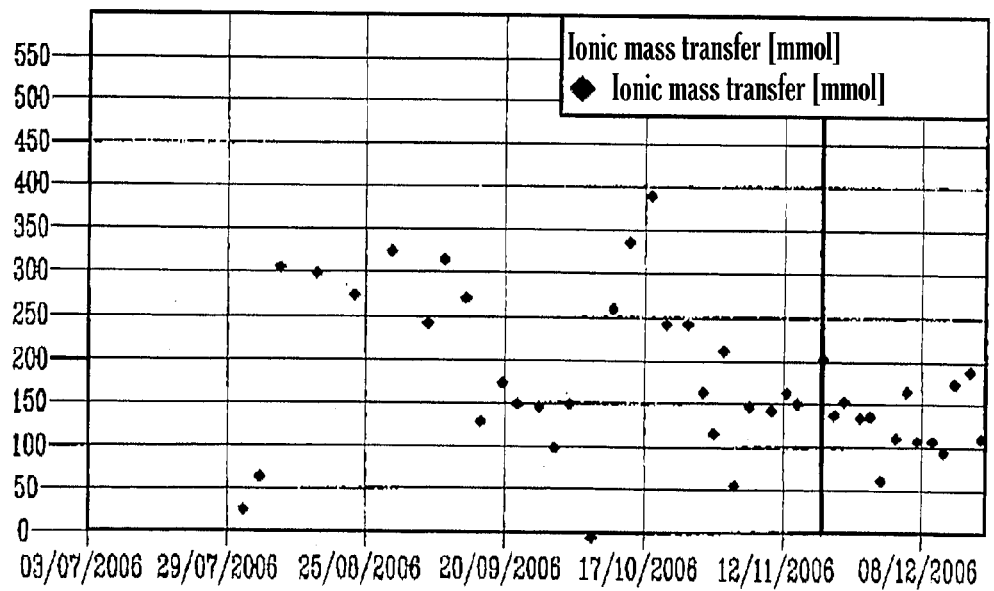
FIGS. 12 and 13 represent examples of evolution over several months of the ionic mass transfer of a patient.
Figure 13:
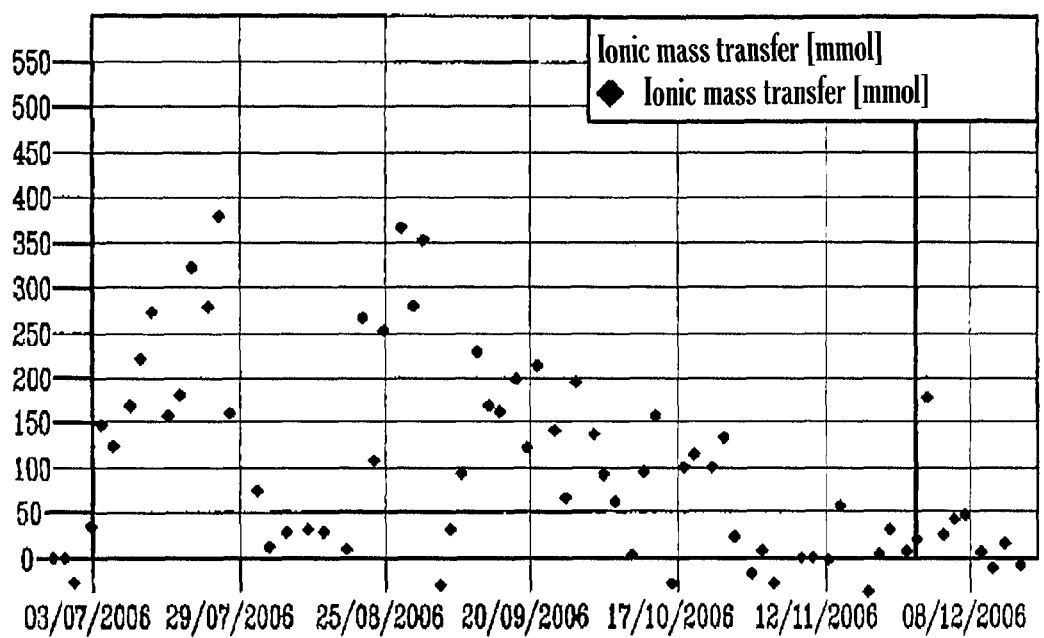

As a matter of fact, as shown in FIGS. 3, 4 and 5, it can be seen that for three different patients stability and evolution are different. In FIG. 3, for the curve of arterial pressure of the patient lying down before the session (lower curve), variability is low and the considered evolution will be taken into account even more. In FIGS. 4 and 5, for the curve of arterial pressure of the patient lying down before the session (lower curve), variability is high and the considered evolution will be taken into account even less.

In the system according to the invention, the programmed means for determining whether the patient falls or not within the first group of hypertension-affected patients are programmed means for determining whether the values representing the evolution of the interdialytic mass of the patient ($\Delta P$) over several sessions (i, j) show a tendency to decrease, the patient being regarded as falling within the first group when the tendency is to decrease.

There is a tendency to decrease of the measured parameter when the general curve of the set of values shows a decrease. This curve can include some values which do not fall within the tendency (about 20%), these values not being taken into account. As a matter of fact, the patient can be out of condition during a session or the parameter can be incorrectly measured.

In the system according to the invention, the means for determining whether the patient falls within the first group of hypertension-affected patients will consider the belonging to the first group when the evolution of the values representing the mass is above about one kilogram.

In the system according to the invention, the programmed means for determining whether the patient falls within the second group of hypertension-affected patients are programmed means for determining whether the values representing the plasmatic conductivity (CP) over several sessions (i, j) show a tendency to increase or furthermore a tendency to decrease, the patient being considered as falling within the second group when the tendency is to increase or furthermore to slightly decrease.

In the system according to the invention, the means for determining whether the patient falls within the second group of hypertension-affected patients will consider the belonging to the second group when the values representing the plasmatic conductivity increase or when the values representing the plasmatic conductivity decrease of less than about 0.3 mS/cm.

The criterion of belonging to the second group is further an evolution of the values representing the plasmatic conductivity which remains stable.

For determining the belonging to the second group, the invention alternatively proposes:
a system wherein the programmed means for determining the non-belonging to the second group of hypertension-affected patients are programmed means for determining whether the values representing the plasmatic conductivity (CP) over several sessions (i, j) show a tendency to decrease.

This system includes programmed means for determining the non-belonging to the second group of hypertension-affected patients when the values representing the plasmatic conductivity decrease of at least about 0.3 mS/cm.

As a matter of fact, if the values representing the plasmatic conductivity (CP) over several sessions (i, j) comply with this tendency to decrease, the patient will be regarded as not falling within the second group. Conversely, the patient will be regarded as falling within the second group.

The criterion of non-belonging to the second group is further complied with when a decrease in the values representing the plasmatic conductivity is stable.

In the system according to the invention, the programmed means for determining whether the patient falls within the third group of hypertension-affected patients are programmed means for determining whether the values representing the ionic mass transfer (TM) over several sessions (i, j) show a tendency to decrease, the third level being regarded as complied with when the tendency is to decrease.

The system according to the preceding section, wherein the means for determining the belonging to the third group of hypertension-affected patients will consider the belonging to the third group when the values representing the plasmatic conductivity decrease of at least about 200 mmol/session.

An additional criterion would consist in that the evolution of the plasmatic conductivity remains stable or shows a tendency to stability.

For the whole invention, the means of determination can be software codes which can take the form of source codes or of codes directly executable on a processor. The means for determining the belonging to a group of hypertensions-affected patients can be subroutines of the score determination means.

In the system according to the invention, for determining the belonging to one of the three groups of hypertension-affected patients, if the number of sessions taken into account is above two, the corresponding means of determination are intended to operate with at least two successive sessions (i, i+1).

In the system according to the invention, for determining the belonging to one of the three groups of hypertension-affected patients, if the number of sessions taken into account is above two, the corresponding means of determination are intended to operate by identifying the first temporal session regarded as anterior session and by identifying the last temporal session regarded as posterior session.

In the system according to the invention, for determining the belonging to one of the three groups of hypertension-affected patients, if the number of sessions taken into account is above two, the corresponding means of determination are intended to regard as temporal sessions those for which the values of at least one parameter taken into account are the most distant.

Spacing of the Sessions Taken into Account:

For the belonging to the groups of hypertension-affected patients, between an anterior session (i) and a posterior session (j), there may be, in terms of number of sessions, ten or indeed several tens of sessions, or, in terms of weeks (at about 3 sessions per week), there may be between 2 weeks and 8 weeks, also between 2 and 6 months.

Generally, the belonging to the groups is determined as a function of the same group of sessions. This group of sessions may stretch between 2 weeks and 6 months, 3 weeks being usually chosen, or else this number of sessions may lie between about ten and several tens.

Generally, nevertheless, it will not be necessary to implement the method of determination according to the invention at each end of treatment session. The user will be able to find an effective monitoring compromise by implementing the method of the invention every three sessions (therefore almost every week) for example, or every six sessions (therefore almost every fortnight).

The system according to the invention can include programmed means for urging or monitoring the change of at least one medical parameter or of at least one machine parameter for each group of hypertension-affected patients. Urging can take place by means of interface means coupled with the calculation and control system, e.g. a display. Monitoring can be carried out by the calculation and control system connected to the necessary hardware.

The system according to the invention can include programmed means for, when the belonging to the first group of hypertension-affected patients is taken into account, suggesting or monitoring during a future session the decrease in the patient's mass that has to be achieved at the end of the session. This mass (or by equivalence weight or any other parameter proportional to these) is known as "dry weight": it is the weight, generally established at the beginning of the dialysis session, which the patient has to achieve at the end of the session. As a rule, the patient's weight is measured at the beginning of the session and, as a function of the dry weight to be achieved, the ultrafiltration means (for instance ultrafiltration pump downstream from the filter on the dialysate side, withdrawing liquid from the extracorporeal circuit) and, if necessary, the liquid injection means (pump on injection line upstream from filter and/or pump on injection line downstream from filter) are controlled as a function of the injected and withdrawn amount of liquid, which is known for instance by calculation or by direct measurement by way of spring balances for the injected liquid and for the liquid withdrawn from the extracorporeal circuit.

The system according to the invention can include the controlled means for suggesting or monitoring said decrease in the patient's mass, which are controlled so that the decrease in the value representing the mass is of at least about 0.5 kg, or about 1 kg.

The system according to the invention can include programmed means for, when the belonging to the second group of hypertension-affected patients is taken into account, suggesting the decrease in the amount of salt taken by the patient from one session to the other.

This salt decrease will be carried out by prescribing to the patient a salt-free or salt-poor diet, which the physician will decide at best depending on the patient.

The system according to the invention can include programmed means for, when the belonging to the third group of hypertension-affected patients is taken into account, suggesting or monitoring during a future session the decrease in the value representing the dialysis conductivity, i.e. the conductivity of the dialysis liquid used during the treatment session.

In the system according to the invention, the suggested or monitored decrease in dialysis conductivity is of at least about 0.2 mmol. Preferably, dialysis conductivity will be decreased of 0.2 mmol for every session from one session to the other over several sessions (it is not deemed as effective to decrease conductivity of too large a value all at one time).

In the system according to the invention, the treatment sessions considered are spread over several sessions over a period of about six months, preferably about 3 months, or about 1 month.

The invention also relates to a computer comprising:
storage means storing at least values of at least one parameter ($P_i$, $P_j$ ... ) representing the mass (P) of the patient, at least values of at least one parameter ($CP_i$, $CP_j$ ... ) representing the patient's plasmatic conductivity, and values of at least one parameter representing the ionic mass transfer ($TM_i$, $TM_j$ ... ) relating to at least one patient undergoing several sessions of extracorporeal blood treatment,
a calculation and control system according to the invention for determining whether the patient whose parametric values of at least one parameter ($P_i$, $P_j$ ... ) representing the mass (P) of the patient, whose values of at least one parameter representing the plasmatic conductivity (CP) and whose values of at least one parameter representing the ionic mass transfer are stored in said storage means, falls or not within a group of hypertension-affected patients.

The invention also relates to an extracorporeal blood treatment machine comprising at least:
a blood treatment unit capable of implementing an extracorporeal blood treatment by blood circulation via an extracorporeal blood circuit comprising an arterial line, a first chamber of a filter separated by a semi-permeable membrane, a venous line, and by dialysate circulation in a second chamber of the filter,
storage means storing at least values of at least one parameter ($P_i$, $P_j$ ... ) representing the mass (P) of the patient, at least values of at least one parameter ($CP_i$, $CP_j$ ... ) representing the patient's plasmatic conductivity, and values of at least one parameter representing the ionic mass transfer ($TM_i$, $TM_j$ ... ) relating to at least one patient undergoing several sessions of extracorporeal blood treatment,
a calculation and control system according to the invention for determining whether the patient whose parametric values of at least one parameter ($P_i$, $P_j$ ... ) representing the mass (P) of the patient, whose values of at least one parameter ($CP_i$, $CP_j$...) representing the patient's plasmatic conductivity and whose values of at least one parameter representing the ionic mass transfer ($TM_i$, $TM_j$ ... ) are stored in said storage means, falls or not within a group of hypertension-affected patients.

The invention further relates to a network comprising:
a server,
at least one blood treatment machine linked to the server, each machine comprising:

means for measuring and/or for calculating medical data relating at least one parameter (Pi, Pj . . . ) representing the mass of the patient, at least one parameter (CPi, CPj . . . ) representing the patient's plasmatic conductivity and at least one parameter representing the ionic mass transfer (TMi, TMj . . . ), means for sending at least part of these measured and/or calculated data to the server, the server comprising:

means for receiving at least part of the medical data relating to extracorporeal blood treatments, storage means for storing the data received from the reception means from one or more blood treatment machines, a calculation and control system according to the invention, intended to operate on the basis of said received data, at least one station (client station for instance) capable of communicating with the server for receiving at least the results of the implementation of said calculation and control system.

The station in the network according to the invention can include a unit for displaying the results relating to the determined group of hypertension-affected patients.

Figure 14:
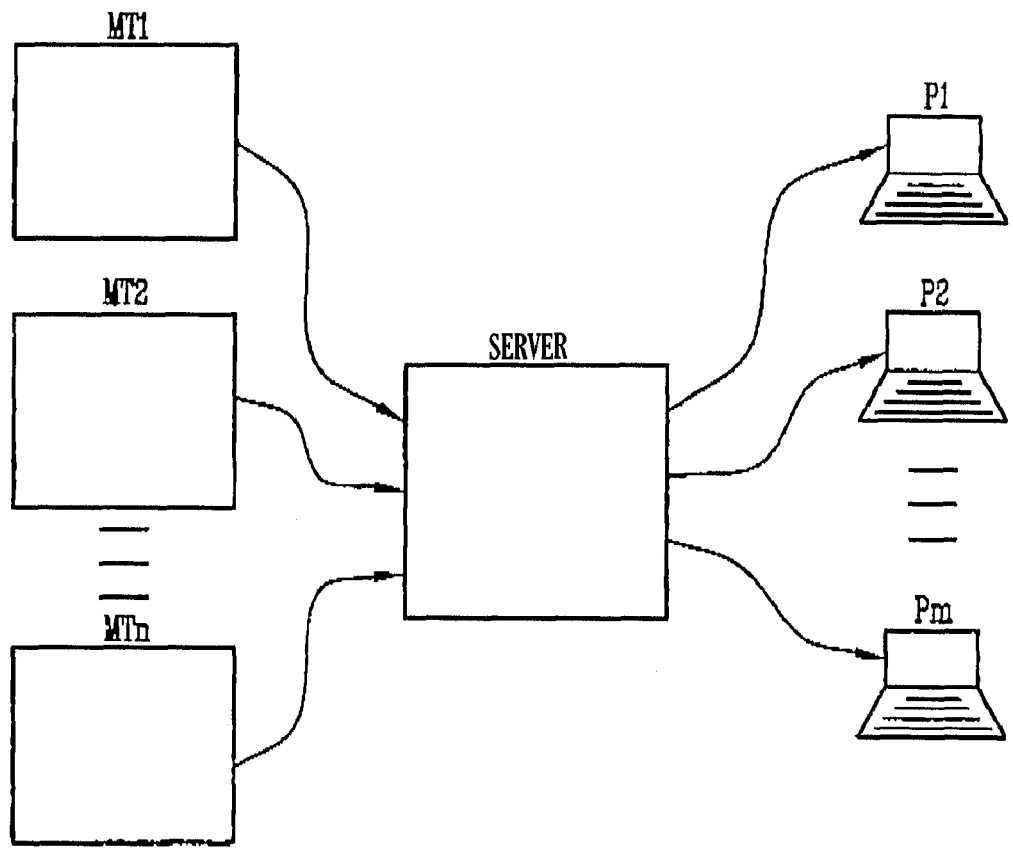
FIGS. 14 and 15 represent a diagram of a complete software and hardware installation according to the invention.
Figure 15:
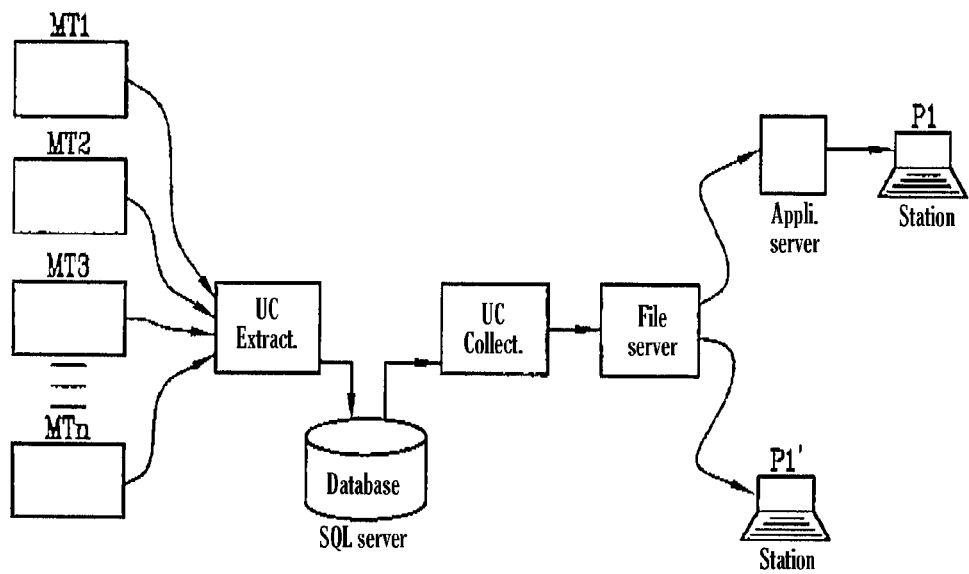

FIGS. 14 and 15 show examples of networks. These networks can comprise a set of elements in the treatment room, another set in the physician's office or in another place where a coordinator works remotely for one or several hospitals.

FIG. 14 shows schematically a group of treatment machines MT1, MT2, . . . MTn placed in a hospital and connected each by cable or wireless link to a server.

This server is able to receive data measured or calculated during and/or after the treatment sessions, is able to store all or part of the data generated by the treatment machine. When only a part of the data is stored, these may have been extracted by a specific collection software for these data. This specific collection software can be integrated into the treatment machine or into the server. This enables to reduce the amount of data to be stored, which is very large due to the number of patients, of parameters and of registered sessions.

Once the necessary parameters have been selected, the server implements the method according to the invention, this method being automated by implementing an expert software.

The user will be able to access at least the results of the method according to the invention via a station connected to said server.

The links described above can be protected by known techniques for reasons of confidentiality of the data relating to a patient. As an alternative or in addition, the data can be "anonymized" before being sent by assigning a code to each patient, without displaying the patient's name during the data exchanges.

The invention also relates to a method for determining whether a patient intended to follow successive sessions (i, j) of extracorporeal blood treatment by extraction and return of the blood falls or not within a group of hypertension-affected patients, the method of determination comprising the following steps:

a) determining the value of at least parameter (Pi, Pj . . . ) representing the mass (P) of the patient for at least two sessions (i, j . . . )

b) determining the value (CPi, CPj, of at least one parameter representing the patient's plasmatic conductivity (CP) for at least two sessions (i, j), c) determining the value (TMi, TMj) of at least one parameter representing the ionic mass transfer of the treatment for at least two sessions (i, j), d) determining whether the patient falls or not within a group of hypertension-affected patients as a function of the evolution over several sessions of at least one of the three following sets of values:

a first set of at least two determined values (Pi, Pj) representing the interdialytic mass of the patient, a second set of at least two determined values (CPi, CPj . . . ) representing the plasmatic conductivity; and a third set of at least two determined values (TMi, TMj) representing the ionic mass transfer.

This method, which is preferably implemented automatically, can be carried out in situ in the treatment room or remotely in a room of the hospital or of a data processing center.

The invention further relates to a computer program for determining whether a patient falls or not within a group of hypertension-affected patients, which program is loadable into the internal memory of a computer, comprising portions of computer program code for, when the program is executed by the computer, implementing the method according to the invention.

This program can be recorded on a readable support in a computer, the support being an optical or magnetic data memory or a volatile memory support.

ADVANTAGES OF THE INVENTION

The invention affords a maximum of advantages of which the main ones are listed here:

swiftness of the determination of a group of hypertension-affected patients, implementation of the invention without necessary additional hardware (medical, hardware, computer . . . ), time saving of additional intervention on the patient, saving of additional labor costs, of consumable medical apparatus, of hardware (use of Doppler . . . ), implementation of the invention without additional manipulation during treatment, and without intervention during dialysis sessions, therefore without causing disturbances, remote monitoring of several patients whose hypertension is detected and/or in one or more hospitals, remote monitoring of a home dialyzed patient by a physician, anticipation of the at risk state of a hypertension-affected patient before the beginning of a dialysis session, to the physician the determined groups can be sent directly and confidentially.

Moreover, the invention relates to a calculation and control system capable of monitoring the vascular access of any patient, including patients that are not affected by hypertension.

This system has been described as a whole in patent application FR0700298 and in patent application PCT/IB2007/000958 issued to the Applicant and incorporated here by reference. Nevertheless, all the features of this aspect of the invention are reminded of in the following, reminding that the invention can take the combined form of a system and/or a method for both determining the belonging to a group of hypertension-affected patients and determining a risk score relating to the vascular access of the patient, as a function of the history of values over several treatment sessions. All the remarks made concerning the determination of the belonging to a group of hypertension-affected patients apply to the aspect of determination of the state of the vascular access.

The invention relates to a calculation and control system for the determination of the state of a vascular access of a patient intended to follow successive sessions (i, j) of extracorporeal blood treatment by extraction and return of the blood via the vascular access, the system comprising the following means:

a) means for determining the value (P1$i$, P1$j$, P2$i$, P2$j$, . . . ) of at least one hemodynamic extracorporeal parameter (P1, P2 . . . ) of the patient for at least two sessions (i, j), b) means for determining the value (Ei, Ej) of the purification effectiveness of the treatment for at least two sessions (i, j), c) programmed means for determining a risk score relating to the state of the vascular access of the patient as a function of said at least two values (Pi, Pj) of the hemodynamic extracorporeal parameter and of said at least two determined values (Ei, Ej) of the purification effectiveness.

The means for determining the value of at least one hemodynamic extracorporeal parameter and the means for determining the value of the purification effectiveness can consist of:

d) at least one memory containing the value of these parameters and that the programmed means will be able to consult to ascertain the chosen values, and/or e) apparatus for detecting the corresponding parameters: pressure detectors or sensors, means for measuring the conductivity or the concentration of a substance in blood, means for measuring dialysance, dialysis dose, clearance, f) a calculation and control unit which will be duly programmed to implement the method according to the invention.

The risk score can take three values:

S0) zero risk score (0) for a patient the state of whose vascular access is normal, s1) intermediate risk score (1) for a patient the state of whose vascular access is doubtful, s2) high risk score (2) for a patient the state of whose vascular access is alarming.

Thus the classification of the risk score of the vascular access can take three different values and gives an appreciation of the patients to be treated immediately by the physician, of the cases with no problem for which the sessions ought to be conducted without modification until the next determination, and of the doubtful or uncertain cases to be monitored or for which it is necessary to go more deeply into the study of the curves measured during the last sessions. The physician, following several tens of patients at the same time, will therefore be able to be steered, on reading the results of the system, very rapidly towards a patient requiring a check or an intervention on his/her vascular access.

Principal Decision Chart:

The system according to the invention has the programmed means for determining the risk score comprising programmed means for determining whether the risk score is high.

The system according to the invention has the programmed means for determining the risk score comprising programmed means for determining whether the risk score is zero.

The system according to the invention has the programmed means for determining the risk score comprising programmed means for, in the case where the risk score is determined neither high nor zero, considering the risk score to be intermediate.

The system according to the invention comprises the programmed means for determining the risk score which are programmed for determining whether the risk score is high before determining whether the risk score is zero.

Figure 16:
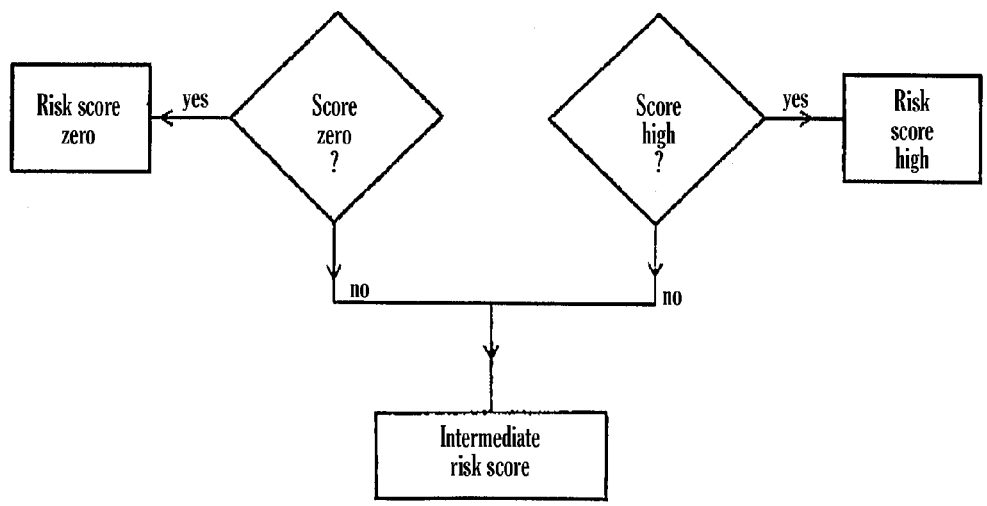
FIG. 16 represents the principal steps of the method for determining the risk score according to the invention.
Figure 17:
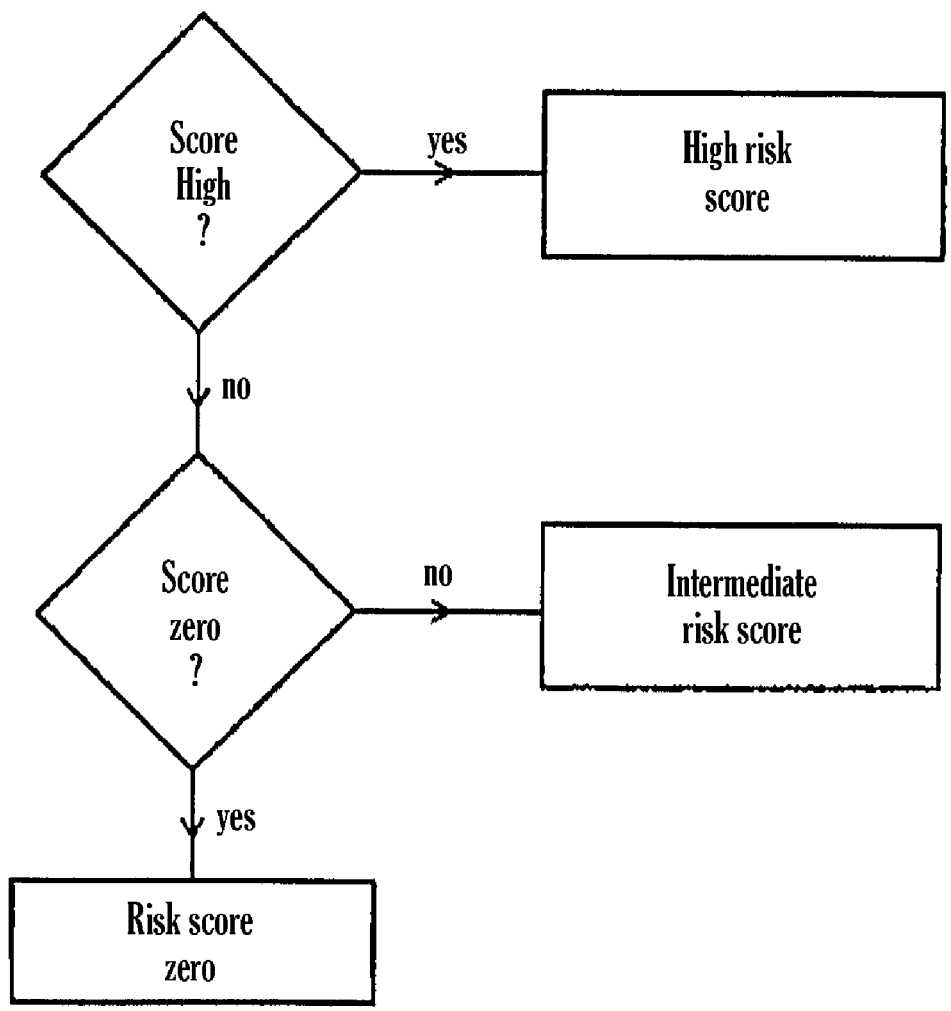
FIG. 17 represents an alternative of the order of the principal steps of the method for determining the risk score.
Figure 18:
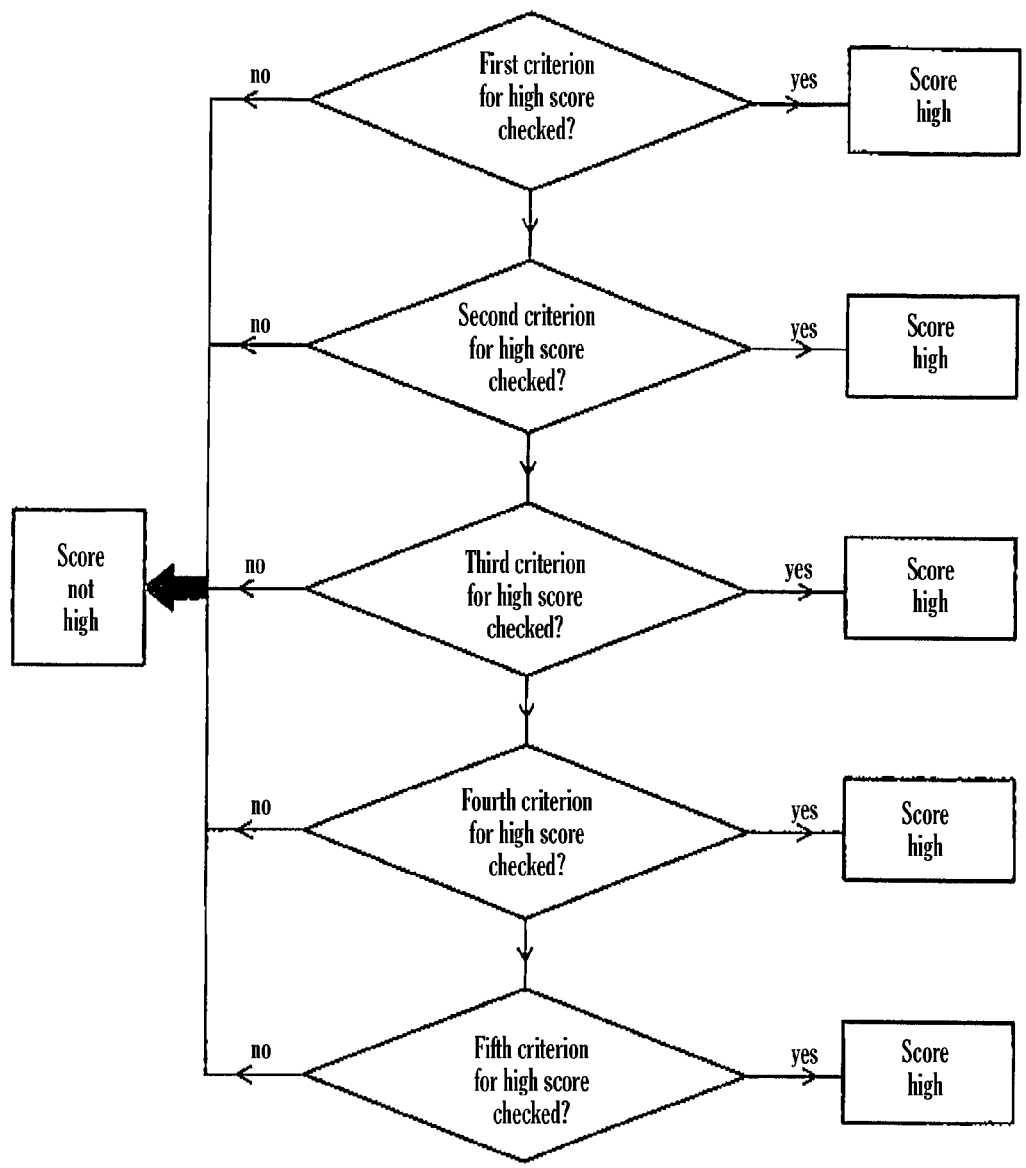
FIG. 18 represents the steps of the determination of the high or non-high risk score according to the invention.
Figure 19:
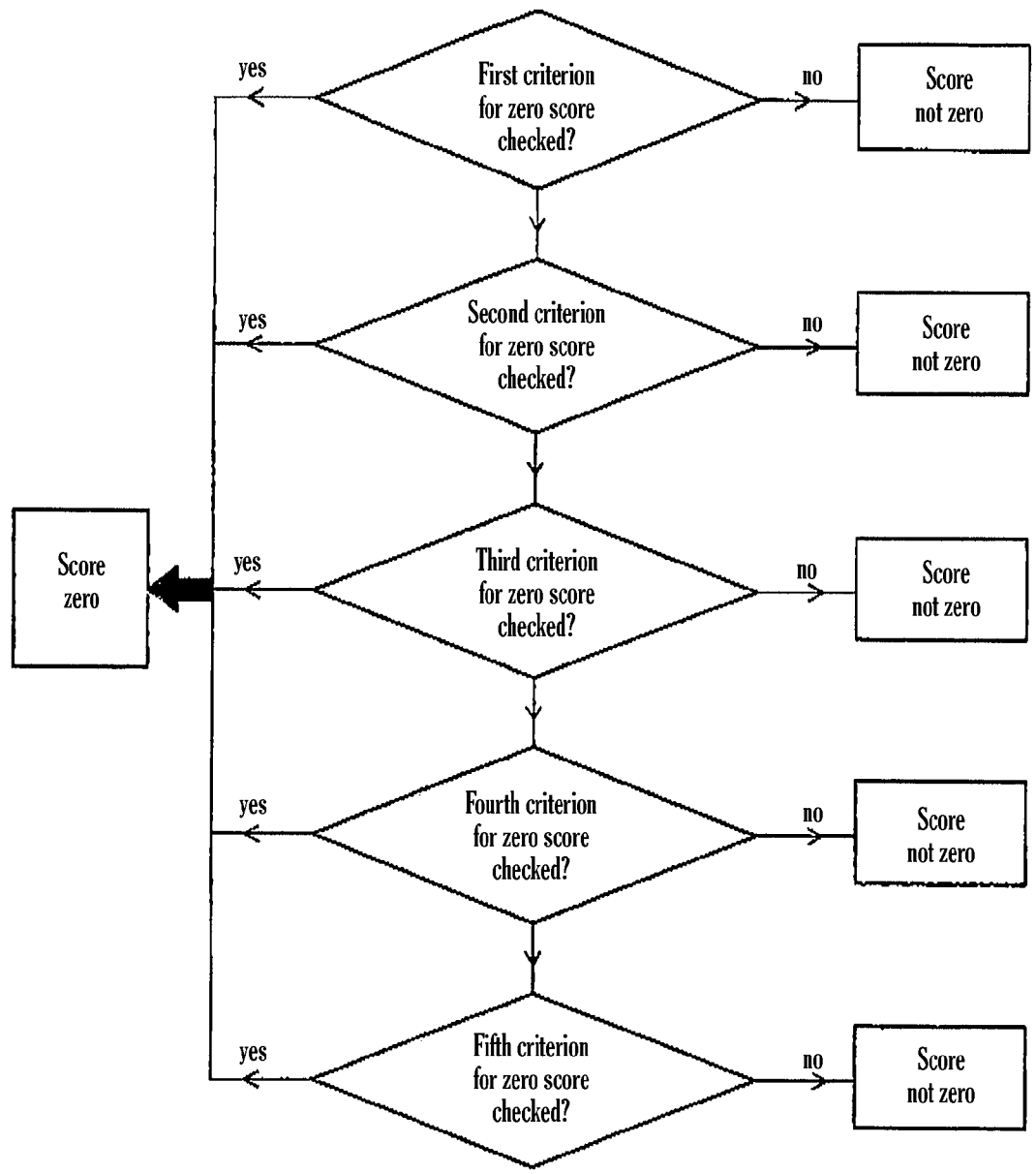
FIG. 19 represents the steps of the determination of the zero or non-zero risk score according to the invention.

As represented in the chart of FIGS. 16 and 17, the invention can comprise:

the determination of the risk score comprises the step of determining whether the risk score is high, the determination of the risk score comprises the additional step of determining whether the risk score is zero, the following additional step: if the risk score is determined to be neither high nor zero, then it is considered as intermediate.

According to a first alternative proposed in the chart of FIG. 16, the steps of determination of the high or non-high score and of determination of the zero or non-zero score can be implemented without temporal condition, simultaneously or otherwise.

According to a second alternative proposed in the chart of FIG. 17, the step of determining whether the risk score is zero is performed after the step of determining whether the risk score is high.

Parameters Involved:

In the system according to the invention, the hemodynamic extracorporeal parameter or parameters (P) have been measured for a session of extracorporeal blood treatment which consists in circulating the blood of the patient at an extracorporeal blood flowrate and in an extracorporeal blood circuit, this circuit comprising an arterial line where there exists an arterial pressure, a filter and a venous line where there exists a venous pressure.

These hemodynamic extracorporeal parameters are chosen from among the group comprising:

extracorporeal venous pressure (Pv), extracorporeal arterial pressure (Pa), extracorporeal blood flowrate of the patient (Qb), a parameter proportional to one of the three aforesaid parameters.

The hemodynamic extracorporeal parameters according to the invention are defined as pertaining to the mechanics of the blood circulation of the extracorporeal cardiovascular system.

The pressures will be measured by pressure sensors positioned on the arterial line and the venous line, the blood flowrate may be considered to be the imposed flowrate of a pump (for example peristaltic) positioned on the arterial line, and/or may be measured by a flowmeter on this line.

These hemodynamic extracorporeal parameters can change on account of the initial vascular access of the patient: for example, the smaller the caliber of the fistula (or central vein, etc.), the more the pressure regime reacts as in front of a difficult vascular access.

These hemodynamic extracorporeal parameters can also change from one session to the other if the same treatment means are not used from one session to the other. It is indeed recommended that the puncture and treatment conditions be standardized by using an identical hemodialyzer, the same access on the arm, the same fistula, the same needle or the same needle diameter, etc. so as to strengthen the reliability of the method. Indeed, the recirculation in the fistula can depend, inter alia, on the extracorporeal blood flowrate, on the position of the needle inserted into the fistula, on the degree of stenosis of the fistula, it is therefore necessary to perform sessions with practices that are as regular as possible.

In the system according to the invention, the purification effectiveness (E) may have been measured for at least one session of extracorporeal blood treatment which consists in circulating the blood of the patient at an extracorporeal blood flowrate and in an extracorporeal blood circuit, this circuit comprising an extracorporeal arterial line, a filter and an extracorporeal venous line, the purification effectiveness (E) being equal to or a function of at least one of the following parameters:

the dialysance (D), or
the clearance (C), or
the concentration of a substance contained in blood upstream from the filter (Cbin), or
the concentration of a substance contained in blood downstream from the filter (Cbout) in the extracorporeal circuit, or
the dialysis dose (KT/v) under the same conditions of session duration, or
a parameter proportional to one of the five aforesaid parameters.

For the person skilled in the art, any physical or chemical parameter giving an indication as to the effectiveness of the transfer across the membrane will be taken into account.

It is necessary to point out that the purification effectiveness is not necessarily calculated during the extracorporeal blood treatment nor during the implementation of the method according to the invention.

An embodiment can have this effectiveness which, once calculated, will be stored in appropriate means. There will thereafter be, after the treatment session for example, during the implementation of the method according to the invention, access to the stored values.

An alternate mode can be the calculation of the effectiveness during treatment, this calculated effectiveness being used immediately for the method according to the invention.

It will be understood that the implementation of the method according to the invention is well separated from the extracorporeal blood treatment.

All this is also valid for the extracorporeal hemodynamic parameters.

Dialysance and Clearance:

The dialysance (D) of a solute is defined as the mass of solute extracted from the blood per time unit divided by the difference between the concentration of this solute in the blood and of this solute in the dialysis liquid, on entry to the dialyzer or filter. This definition in general applies when the solute is present in the blood and in the fresh dialysis liquid (before entering the filter and contacting the blood via the semi-permeable membrane), or when the solute is present in the blood only. We shall for example speak in the first case of dialysance of sodium, of calcium or for example in the second case of dialysance of urea or of beta-2 microglobulin. The clearance of a solute is a particular case of the dialysance of a solute. It is the dialysance when the solute is present in the blood only and consequently is absent from the fresh dialysis liquid: we shall speak of urea clearance.

The dialysance or clearance of a solute can be calculated in different ways: on-line in the extracorporeal circuit during the treatment or after the treatment, in-vivo during the treatment or after the treatment, once or several times by periodic samples, etc.

Patent EP 0547025, incorporated here by way reference, explains one mode of calculating the dialysance among others. As a reminder, it involves a procedure for determining a concentration of a substance in the blood of a patient undergoing a dialysis treatment in an artificial kidney (or filter or dialyzer) and/or the actual dialysance for said substance of the artificial kidney, the artificial kidney comprising an extracorporeal blood circuit connected to a dialyzer having a semipermeable membrane which delimits a first compartment for blood circulation and a second compartment for the circulation of a dialysis liquid on the other side of the membrane, characterized by the steps of:

circulating successively in the second compartment of the dialyzer, a first and a second liquid only differing in the concentration of the substance,
measuring, in the first and second dialysis liquids, the conductivity or the concentration of the substance upstream and downstream from the dialyzer, and
calculating, on the basis of the conductivity (by a conductimeter) or of the measured concentration of the substance in the first and second dialysis liquids, the concentration of the substance in the blood on entry to the dialyzer and/or the actual dialysance of the artificial kidney.

Dialysis Dose:

The total dialysis dose delivered is the integral of the values of average clearance or dialysance measured over a determined time interval.

The dialysis dose administered after a treatment time t can be regarded, according to the work of Sargent and Gotch, as the dimensionless ratio Kt/V, wherein K is the real clearance for the urea, t the elapsed treatment time, and V the volume of distribution of the urea, that is to say the total water volume of the patient (Gotch F A, Sargent S A. *A mechanistic analysis of the National Cooperative Dialysis Study (NCDS). Kidney int* 1985; 28: 526-34).

Patent EP0920877, incorporated here by way of reference, explains another mode of calculating a parameter representing the effectiveness of the treatment, for example dialysance, clearance, dialysis dose or another parameter representing the effectiveness of an extracorporeal blood treatment.

In the system according to the invention, the values of the hemodynamic extracorporeal parameter or parameters and of the purification effectiveness can be average values of these parameters over a treatment session.

These values can alternatively be an instantaneous value chosen at a time t of the session, at the beginning, in the middle or at the end of the session, or can also be a mean value, or any other mathematical value representing as accurately as possible the parameter or its evolution over a dialysis session.

Determination of the High Risk Score (2):

The system according to the invention has the programmed means for determining a high score comprising at least one from among the following means:

programmed means for determining a first high score criterion,
programmed means for determining a second high score criterion,
programmed means for determining a third high score criterion,
programmed means for determining a fourth high score criterion,
programmed means for determining a fifth high score criterion, and wherein the programmed means for determining whether the score is high are capable of sending as result:

a high score when at least one from among five criteria of high risk score is fulfilled,
a non-high score when all the five criteria of high risk score are not fulfilled.

Specifically, if a single one among the 5 high score criteria is fulfilled, this suffices to deduce therefrom the high risk score.

It will also be possible to envisage a level of high risk score as a function of the number of high score criteria fulfilled. The more a patient has high score criteria fulfilled, the more the attention to this patient will take priority. The priority of the high risk score may also be calculated and employed for the presentation of the results to the physician.

Figure 2:
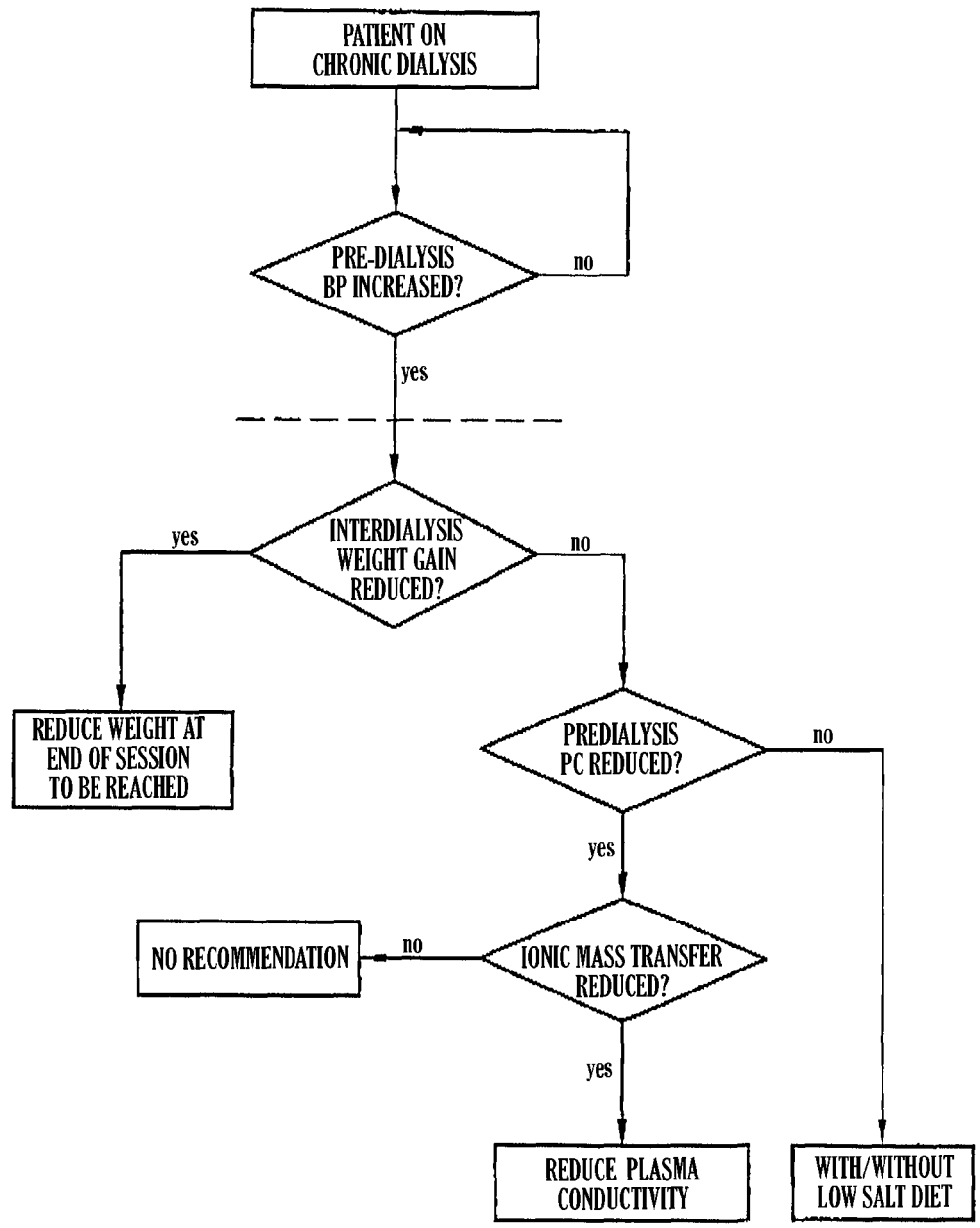

Score Criteria:

It should be noted generally that, despite the step by step schematization of the chart of FIGS. 2 and 3, the fulfilment of the five high score criteria and of the six zero score criteria can be performed simultaneously and without imposition as regards the temporal order in which they are fulfilled. The graphical representation is done only for the sake of clarity.

We shall examine in detail each of the five criteria of high risk score.

First Criterion of High Risk Score (2):

This involves determining whether a first criterion of high risk score is or is not satisfied.

According to the invention, the system has the programmed means for determining a first criterion of high risk score which are intended to operate at least as a function of the effectiveness parameters ($P1i$, $P1j$, $P2i$, $P2j$ . . . ), and of the extracorporeal blood flowrate ($Qbi$, . . . , $Qbj$) determined for at least two sessions.

More particularly, the programmed means for determining the first criterion of high risk score can be intended at least to compare, for at least two sessions, each value of the effectiveness parameter ($Ei$, . . . , $Ej$) of a session with a linear function of the value of the extracorporeal blood flowrate ($Qbi$, . . . , $Qbj$) of the same session.

More particularly, the programmed means for determining the first satisfied high risk criterion can be intended to determine for at least two sessions whether each value of the determined effectiveness ($E(i)$) of a session lies on or below the straight line of equation:

$$E(i)=0.4*Qb(i)+40,$$

with $Qb(i)$ being the blood flowrate of the patient for the same session (i);
the score being high if this criterion is satisfied.

Specifically, the equation of this straight line corresponds to the following exemplary values:

For Qsg=250 ml/min, the effectiveness ought to be equal to or greater than 140.
For Qsg=300 ml/min, the effectiveness ought to be equal to or greater than 160.
For Qsg=350 ml/min, the effectiveness ought to be equal to or greater than 180.
For: Qsg=400 ml/min, the effectiveness ought to be equal to or greater than 200.

Generally throughout the present application, it should be noted that it involves values calculated for the given straight line equations, but that these compared data correspond to numerical values, since the units are not complied with.

Second Criterion of High Risk Score:

This involves determining whether a second high score criterion is or is not satisfied.

According to the invention, the system has the programmed means for determining a second criterion of high risk score which can be intended to operate at least as a function of the values of the venous pressure ($Pvi$, . . . , $Pvj$) and of the arterial pressure ($Pai$, . . . , $Paj$) determined for at least two sessions.

More particularly, the programmed means for determining the second criterion of high risk score can be intended to compare, for at least two sessions, the arterial pressure value and the venous pressure value, respectively, of a session with a predetermined arterial pressure value and a predetermined venous pressure value, respectively.

More particularly, the system has the programmed means for determining the second criterion of high risk score that can be intended to determine for at least two sessions (i, j) whether:

the value of the venous pressure ($Pv(i)$, . . . , $Pv(j)$) is greater than or equal to 250 mmHg, and
the value of the arterial pressure ($Pa(i)$, . . . , $Pa(j)$) is less than −200 mmHg, the score being high if both these conditions are satisfied.

The threshold values can of course vary in an interval about the values indicated, as a function of the patient, for example. A threshold value of venous pressure may lie between 200 and 300, about 250 preferably.

The larger the number of sessions for which this first criterion examined is satisfied, the surer the result obtained for this criterion.

Third Criterion of High Risk Score:

This involves determining whether a third high score criterion is or is not satisfied.

According to the invention, the system has the programmed means for determining a third criterion of high risk score which can be intended to operate at least as a function of the evolution of the values of venous pressure ($Pv(j)-Pv(i)$), of the evolution of the values of arterial pressure ($Pa(j)-Pa(i)$) and of the evolution of the effectiveness values ($E(j)-E(i)$) determined between an anterior session (i) and a posterior session (j).

More particularly, the system has the programmed means for determining the third criterion of high risk score which can be intended to:

compare the evolution of the effectiveness ($E(j)-E(i)$) in relation to the value of the effectiveness of the anterior session ($E(i)$), and
compare the evolution of the arterial pressure ($Pa(j)-Pa(i)$) and venous pressure ($Pv(j)-Pv(i)$) with a predetermined value.

More particularly, the system has the programmed means for determining the third criterion of high risk score which can be intended to determine whether:

the absolute value of the variation in the effectiveness ($E(j)-E(i)$) between the anterior session (i) and the posterior session (j) is greater than or equal to 10%, preferably 20%, of the value of the effectiveness of the anterior session ($E(i)$), and
the increase in the venous pressure ($Pv(j)-Pv(i)$) between the anterior session (i) and the posterior session (j) is greater than or equal to 50 mmHg, and
the decrease in the arterial pressure ($Pa(j)-Pa(i)$) between the anterior session (i) and the posterior session (j) is less than or equal to 50 mmHg, the score being high if these three conditions are satisfied.

The threshold value of 50 mmHg is an indicative value, but the threshold can vary and be fixed onwards of 40 mmHg. This value can be chosen by the physician as a function of the usual arterial or venous pressure of the patient. The same applies to the threshold percentage of the variation in the effectiveness.

Fourth Criterion of High Risk Score:

This involves determining whether a fourth high score criterion is or is not satisfied.

According to the invention, the system has the programmed means for determining a fourth criterion of high risk score which can be intended to operate at least as a function of the evolution of the values of venous pressure (Pv(j)−Pv(i)), of the evolution of the values of arterial pressure (Pa(j)−Pa(i)) and of the evolution of the effectiveness values (E(j)−E(i)) determined between an anterior session (i) and a posterior session (j).

More particularly, the system has the programmed means for determining the fourth criterion of high risk score which can be intended to compare each of said three parametric evolutions in relation to the value of the parameter of the anterior session.

More particularly, the system has the programmed means for determining the fourth criterion of high risk score which can be intended to determine whether:
  the increase in the venous pressure (Pv(j)−Pv(i)) between the anterior session (i) and the posterior session (j) is greater than or equal to 10%, preferably 20% of the value of the venous pressure of the anterior session (Pv(i)), and
  the decrease in the arterial pressure (Pa(j)−Pa(i)) between said sessions is greater than or equal to 10%, preferably 20% of the value of the arterial pressure (Pv(i)) of the anterior session,
the score being high if these two conditions are satisfied.

The threshold percentage value given is an indicative value, but the threshold can vary and be fixed between 10% and 20%. This value can be chosen by the physician as a function of the usual arterial or venous pressure of the patient.

Fifth Criterion of High Risk Score:

This involves determining whether a fifth high score criterion is or is not satisfied.

The system according to the invention has the programmed means for determining the fifth criterion of high risk score which can be intended to operate at least as a function of the evolution of the purification effectiveness (E(i)−E(j)) between an anterior session (i) and a posterior session (j).

More particularly, the system has the programmed means for determining the fifth criterion of high risk score which can be intended to compare the evolution of the purification effectiveness (E(i)−E(j)) with a predetermined value.

More particularly, the system has the programmed means for determining the fifth criterion of high risk score which can be intended to determine whether the decrease in the purification effectiveness (E(i)−E(j)) between the anterior session (i) and the posterior session (j) is greater than or equal to 40 ml/min, the score being high if this condition is satisfied.

The threshold value of 40 ml/min is an indicative value, but the threshold can vary and be fixed onwards of 30 ml/min. This value can be chosen by the physician as a function of the usual purification effectiveness in the patient.

Moreover, according to the invention:
  for the determination of the first criterion of high risk score, if the number of sessions considered is greater than two, the corresponding means of determination are intended to operate with each session considered;
  for the determination of the second criterion of high risk score, if the number of sessions considered is greater than two, the corresponding means of determination are intended to operate with at least two successive sessions (i, i+1);
  for the determination of at least one from among the third, fourth and fifth criteria of high risk score, if the number of sessions considered is greater than two, the corresponding means of determination are intended to operate by identifying the first temporal session considered as anterior session and by identifying the last temporal session considered as posterior session;
  for the determination of at least one from among the third, fourth and fifth criteria of high risk score, if the number of sessions considered is greater than two, the corresponding means of determination are intended to consider as temporal sessions those for which the values of at least one parameter considered are the most distant.

It may nevertheless also be valid to consider more than two sessions so as to discern the evolution from one session to another.

Determination of Zero Risk Score (0):

The system according to the invention comprises programmed means for determining the zero risk score comprising:
  programmed means for determining a first zero score criterion,
  programmed means for determining a second zero score criterion,
  programmed means for determining a third zero score criterion,
  programmed means for determining a fourth zero score criterion,
  programmed means for determining a fifth zero score criterion,
  programmed means for determining a sixth zero score criterion,
and wherein the programmed means for determining whether the score is zero are capable of sending as result:
  a zero score when six criteria of zero risk score are all fulfilled, or
  a non-zero score when at least one from among the six zero score criteria is not fulfilled.

First Criterion of Zero Risk Score:

This involves determining whether a first criterion of zero risk score is or is not satisfied.

According to the invention, the programmed means for determining a first criterion of zero risk score can be intended to operate at least as a function of the effectiveness parameter (E(i), . . . , E(j)) and of the extracorporeal blood flowrate (Qb(i), . . . , Qb(j)) determined for at least two sessions.

More particularly, the programmed means for determining the first criterion of zero risk score can be intended to compare, for at least two sessions, each value of the effectiveness parameter (E(i), . . . , E(j)) of a session with a linear function of the value of the extracorporeal blood flowrate (Qb(i), . . . , Qb(j)) of the same session.

More particularly, the programmed means for determining the first zero risk criterion can be intended to determine, for at least two sessions, whether each value of the determined effectiveness of a session lies on or above the straight line of equation:

$$E(i)=0.4*Qb(i)+40,$$

with Qb(i) being the extracorporeal blood flowrate for the same session (i), the first criterion of zero risk score being satisfied in this case.

The larger the number of sessions for which this first (or any other) criterion examined is satisfied, the surer the result obtained for this criterion.

Specifically, the equation of this straight line corresponds to the following exemplary values:

For Qb=250 ml/min, the effectiveness ought to be equal to or greater than 140.

For Qb=300 ml/min, the effectiveness ought to be equal to or greater than 160.

For Qb=350 ml/min, the effectiveness ought to be equal to or greater than 180.

For: Qb=400 ml/min, the effectiveness ought to be equal to or greater than 200.

Second Criterion of Zero Risk Score:

This involves determining whether a second criterion of zero risk score is or is not satisfied.

According to the invention, the system comprises programmed means for determining a second criterion of zero risk score which are intended to operate at least as a function of the values of the venous pressure (Pv(i), ..., Pv(j)) and of the arterial pressure (Pa(i), ..., Pa(j)) and of the values of the blood flowrate of the patient (Qb(i), ..., Qb(j)) determined for at least two sessions.

More particularly, the programmed means for determining a second criterion of zero risk score can be intended to compare, for at least two sessions, each value of the arterial pressure (Pa(i), ..., Pa(j)) with a linear function of the blood flowrate (Qb(i), ..., Qb(j)) of the session and each value of the venous pressure value (Pv(i), ..., Pv(j)) with a linear function of the blood flowrate of the session (Qb(i), ..., Qb(j)).

More particularly, the programmed means for determining the second criterion of zero risk score can be intended to determine for at least two sessions (i, j):
- whether each absolute value of the arterial pressure (Pa(i), ..., Pa(j)) determined per session is less than or equal to half the blood flowrate of the patient (Qb(i), ..., Qb(j)) for the session considered (i, ..., j), and
- whether each value of the venous pressure (Pv(i), ..., Pv(j)) determined per session is less than or equal to half the blood flowrate of the patient (Qb(i), ..., Qb(j)) for the session considered (i, ..., j), the second criterion of zero risk score being satisfied in this case.

Specifically, the equation of this straight line corresponds to the following exemplary values:

For Qb=250 ml/min, the venous pressure ought to be less than or equal to 125 mmHg and the arterial pressure ought to be greater than or equal to −125 mmHg.

For Qb=300 ml/min, the venous pressure ought to be less than or equal to 150 mmHg and the arterial pressure ought to be greater than or equal to −150 mmHg.

For Qb=350 ml/min, the venous pressure ought to be less than or equal to 175 mmHg and the arterial pressure ought to be greater than or equal to −175 mmHg.

For Qb=400 ml/min, the venous pressure ought to be less than or equal to 200 mmHg and the arterial pressure ought to be greater than or equal to −200 mmHg.

Third Criterion of Zero Risk Score:

This involves determining whether a third criterion of zero risk score is or is not satisfied.

According to the invention, the system comprises programmed means for determining the third criterion of zero risk score which can be intended to operate at least as a function of the evolution of the extracorporeal blood flowrate (Qb(j)−Qb(i)) between an anterior session (i) and a posterior session (j).

More particularly, the programmed means for determining the third criterion of zero risk score can be intended to compare the evolution of the blood flowrate of the patient (Qb(j)−Qb(i)) with a predetermined value.

More particularly, the programmed means for determining the third criterion of zero risk score can be intended to determine whether the absolute value of the variation in the blood flowrate (|Qb(j)−Qb(i)|) between an anterior session (i) and a posterior session (j) is less than or equal to 20 ml/min, the third criterion of zero risk score being satisfied in this case.

The threshold difference value of 20 ml/min is an indicative value, but the threshold can vary and be fixed onwards of 10 ml/min. This value can be chosen by the physician as a function of the usual blood flowrate of the patient during treatment, and would vary between 10 and 20, or greater than 20.

Fourth Criterion of Zero Risk Score:

This involves determining whether a fourth criterion of zero risk score is or is not satisfied.

According to the invention, the system comprises programmed means for determining the fourth criterion of zero risk score which can be intended to operate at least as a function of the evolution of the values of arterial pressure (Pa(j)−Pa(i)) between an anterior session (i) and a posterior session (j).

More particularly, the programmed means for determining the fourth criterion of zero risk score can be intended to compare the evolution of the arterial pressure (Pa(j)−Pa(i)) with the value of arterial pressure of the anterior session (Pa(i)).

More particularly, the programmed means for determining the fourth criterion of zero risk score can be intended to determine whether the variation in the arterial pressure (Pa(j)−Pa(i)) between the anterior session (i) and the posterior session (j) is less than or equal to 10%, preferably to 20%, of the arterial pressure (P(i)) of the anterior session, the fourth criterion of zero risk score being satisfied in this case.

The threshold percentage value given is an indicative value, but the threshold can vary and be fixed between 10% and 20%. This value can be chosen by the physician as a function of the usual arterial pressure of the patient.

Fifth Criterion of Zero Risk Score:

This involves determining whether a fifth criterion of zero risk score is or is not satisfied.

According to the invention, the system comprises programmed means for determining the fifth criterion of zero risk score which can be intended to operate at least as a function of the evolution of the values of venous pressure ((Pv(j)−Pv(i)) between an anterior session and a posterior session.

More particularly, the programmed means for determining the fifth criterion of zero risk score can be intended to compare the evolution of the venous pressure ((Pv(j)−Pv(i)) with the value of the venous pressure of the anterior session (Pv(i)).

More particularly, the programmed means for determining the fifth criterion of zero risk score can be intended to determine whether the variation in the venous pressure ((Pv(j)−Pv(i)) between the anterior session (i) and the posterior session (j) is less than or equal to 10%, preferably to 20%, of the venous pressure (Pv(i)) of the anterior session, the fifth criterion of zero risk score being satisfied in this case.

The threshold percentage value given is an indicative value, but the threshold can vary and be fixed between 10% and 20%. This value can be chosen by the physician as a function of the usual venous pressure of the patient.

Sixth Criterion of Zero Risk Score:

This involves determining whether a sixth criterion of zero risk score is or is not satisfied.

According to the invention, the system comprises programmed means for determining the sixth criterion of zero risk score which can be intended to operate at least as a function of the evolution of the effectiveness of the treatment ((E(j)−E(i)) between an anterior session (i) and a posterior session (j).

More particularly, the programmed means for determining the sixth criterion of zero risk score can be intended to compare the evolution of the effectiveness ((E(j)−E(i)) of the treatment with a predetermined value.

More particularly, the programmed means for determining a sixth criterion of zero risk score can be intended to determine whether the absolute value of the variation in the effectiveness of the treatment ((E(j)−E(i)) between the anterior session (i) and the posterior session (j) is less than or equal to 10 ml/min, the sixth criterion of zero risk score being satisfied in this case.

The threshold value of 10 ml/min is an indicative value, but the threshold can vary and be fixed onwards of 5 ml/min. This value can be chosen by the physician as a function of the usual purification effectiveness in the patient.

In the system according to the invention:
for the determination of at least one from among the first and the second criteria of zero risk score, if the number of sessions considered is greater than two, the corresponding means of determination are intended to operate with each session considered;
for the determination of at least one from among the third, fourth, fifth and sixth criteria of zero risk score, if the number of sessions considered is greater than two, the corresponding means of determination are intended to operate by identifying the first temporal session considered as anterior session and by identifying the last temporal session considered as posterior session;
for the determination of at least one from among the third, fourth, fifth and sixth criteria of zero risk score, if the number of sessions considered is greater than two, the corresponding means of determination are intended to consider as temporal sessions those for which the values of at least one parameter considered are the most distant.

In the system according to the invention, the treatment sessions considered are spread over at least two weeks, preferably over an interval lying between two weeks and six months, more preferably over an interval of three weeks.

System for Determining Reliability of Risk Score:

The invention pertains to a system for determining reliability of risk score of the state of a vascular access comprising the following means:
the system for determining the state of a vascular access described above,
means for storing:
I. a first risk score (S) determined over a first time interval defined between an anterior session and a posterior session and comprising more than two sessions,
II. at least one second risk score (S') determined over at least one second time interval situated inside the first determined interval,
programmed means for calculating the reliability as a function of the first score determined and at least of the second score determined (S, S').

More particularly, when a number n of risk scores is determined by the system for determining the state of a vascular access, the programmed means for calculating the reliability can be intended to calculate the reliability percentage as equal or related to the ratio of the number of identities between the first risk score determined over the first interval and each of the other risk scores determined over an interval inside the first interval divided by the number n.

Particularly, the second time interval can have as posterior bound the posterior session of the first interval, or a bound temporally very close to the posterior bound the posterior session of the first interval.

It should be clearly noted that the system according to the invention is not necessarily implemented during the treatment. Preferably, it is implemented after a treatment session, if the parameters considered are mean parameters over a session.

The invention also relates to a computer comprising:
storage means storing at least values of at least one extracorporeal hemodynamic parameter (P1$i$, ..., P1$j$, ... P2$i$, ..., P2$j$ ...) and purification effectiveness values (E(i), ..., E(j)) relating to at least one patient subjected to several sessions (i, ... j) of extracorporeal blood treatment,
a calculation and control system according to the invention for the determination of the vascular state of the patient the parametric values of at least one of whose extracorporeal hemodynamic parameters (P1$i$, ..., P1$j$, ... P2$i$, ..., P2$j$ ...) and whose purification effectiveness values (E(i), ..., E(j)) are stored in said storage means.

The invention also relates to an extracorporeal blood treatment machine comprising at least:
a blood treatment unit capable of implementing an extracorporeal blood treatment by blood circulation via an extracorporeal blood circuit comprising an arterial line, a first chamber of a filter separated by a semi-permeable membrane, a venous line, and by dialysate circulation in a second chamber of the filter,
storage means storing at least values of at least one extracorporeal hemodynamic parameter and purification effectiveness values relating to at least one patient subjected to several sessions of extracorporeal blood treatment,
a calculation and control system according to the invention for the determination of the vascular state of the patient the parametric values of at least one of whose extracorporeal hemodynamic parameters (P1$i$, ..., P1$j$, ... P2$i$, ..., P2$j$ ...) and whose purification effectiveness values (E(i), ..., E(j)) are stored in said storage means.

The invention also relates to a network comprising:
a server,
at least one blood treatment machine linked to the server, each machine comprising:
means for measuring and/or for calculating medical data relating to at least one extracorporeal hemodynamic parameter (P1$i$, ..., P1$j$, ... P2$i$, ..., P2$j$ ...) and to the purification effectiveness of the treatment (E(i), ..., E(j)),
means for sending at least part of these measured and/or calculated data to the server,
the server comprising:
means for receiving at least part of the medical data relating to extracorporeal blood treatments,
storage means for storing the data received by the reception means from one or more blood treatment machines,
a calculation and control system according to the invention, intended to operate on the basis of said received data,
at least one station (client station for example) capable of communicating with the server for receiving at least the results of the implementation of said calculation and control system.

The station can comprise a unit for displaying the risk score results.

This method is described during the treatment, but can be implemented after the treatment and in a distant place for the selection step (as in FIG. 15).

Once the necessary parameters have been selected, the server implements the method according to the invention, this method being automated by the implementation of expert software.

The user will be able to access at least the results of the method according to the invention via a station linked to said server.

The links described can be protected by known techniques for reasons of confidentiality of the data relating to a patient. Alternatively or additionally, the data can be, before sending, "anonymized" by the allocation of a code to each patient, without displaying the name of the patient during the data exchanges.

Also, the invention relates to a method for determining the state of a vascular access of a patient intended to follow successive sessions (i, j) of extracorporeal blood treatment by extraction and return of the blood via the vascular access, the method of determination comprising the following steps:

a) determining the value (Pi, Pj) of at least one hemodynamic extracorporeal parameter (P) of the patient for at least two sessions (i, j),
b) determining the value (Ei, Ej) of the purification effectiveness of the treatment for at least two sessions (i, j),
c) determining a risk score relating to the state of the vascular access of the patient as a function of said at least two values (Pi, Pj) of the hemodynamic extracorporeal parameter and of said at least two determined values (Ei, Ej) of the purification effectiveness.

This method, which is preferably implemented automatically, can be carried out in situ in the treatment room or remotely in a room of the hospital or of a data processing center.

In the method according to the invention, the risk score can take three values:

s0) zero risk score for a patient the state of whose vascular access is normal,
s1) intermediate risk score for a patient the state of whose vascular access is uncertain (or "doubtful"),
s2) high risk score for a patient the state of whose vascular access is alarming.

The determination of the risk score can comprise:
the step of determining whether the risk score is high,
the additional step of determining whether the risk score is zero,
the following additional step: if the risk score is determined neither alarming nor zero, then it is considered intermediate.

The step of determining whether the risk score is zero can be performed after the step of determining whether the risk score is high.

Parameters Involved:

In the method according to the invention, the hemodynamic extracorporeal parameter or parameters (P) have been measured for a session of extracorporeal blood treatment which consists in circulating the blood of the patient at an extracorporeal blood flowrate and in an extracorporeal blood circuit, this circuit comprising an arterial line where there exists an arterial pressure, a filter and a venous line where there exists a venous pressure.

These parameters can be chosen from among the group comprising:
extracorporeal venous pressure (Pv),
extracorporeal arterial pressure (Pa),
extracorporeal blood flowrate of the patient (Qb),
a parameter proportional to one of the three aforesaid parameters.

In the method according to the invention, the purification effectiveness (E) has been measured for a session of extracorporeal blood treatment which consists in circulating the blood of the patient at an extracorporeal blood flowrate and in an extracorporeal blood circuit, this circuit comprising an extracorporeal arterial line, a filter and an extracorporeal venous line, the purification effectiveness (E) being equal or a function of at least one of the following parameters:
the dialysance (D), or
the clearance (C), or
the concentration of a substance contained in blood upstream from the filter (Cbin), or
the concentration of a substance contained in blood downstream from the filter (Cbout) in the extracorporeal circuit, or
the dialysis dose (KT/v), or
a parameter proportional to one of the five aforesaid parameters.

The values of the hemodynamic parameter or parameters and of the purification effectiveness can be the average values of these parameters over a treatment session.

All the remarks made for the devices according to the invention are also valid for the method according to the invention.

Determination of the High Risk Score (2):

The method according to the invention comprises the step of determining if the score is high having:
as result a high score when at least one from among five criteria of high risk score is fulfilled,
as result a non-high score when all the five criteria of high risk score are not fulfilled.

Determination of the First Criterion of High Risk Score:

According to the invention, the determination of a first criterion of high risk score is at least a function of the effectiveness parameter and the extracorporeal blood flowrate determined for at least two sessions.

More particularly, the determination of the first criterion of high risk score is performed at least by comparing, for at least two sessions, each value of the effectiveness parameter of a session with a linear function of the value of the extracorporeal blood flowrate of the same session.

More particularly, the determination of the first satisfied high risk criterion consists in determining for at least two sessions whether each value of the determined effectiveness of a session lies on or below the straight line of equation:

$$E(i) = 0.4 * Qb(i) + 40,$$

with Qb(i) being the blood flowrate of the patient for the same session (i); the score being high if this criterion is satisfied.

The larger the number of sessions for which this first criterion examined is satisfied, the surer the result obtained for this criterion.

Second Criterion of High Risk Score:

According to the invention, the determination of a second criterion of high risk score is at least a function of the values of the venous pressure and the arterial pressure determined for at least two sessions.

More particularly, the determination of the second criterion of high risk score is made by comparing, for at least two sessions, the arterial pressure value and the venous pressure value, respectively, of a session with a predetermined arterial pressure value and a predetermined venous pressure value, respectively.

More particularly, the determination of the second criterion of satisfied high risk score consists in determining for at least two sessions (i, j) whether:

the value of the venous pressure (Pv(i), Pv(j)) is greater than or equal to 250 mmHg, and the value of the arterial pressure (Pa(i), Pa(j)) is less than −200 mmHg for at least two sessions (i, j);

the score being high if these two conditions are satisfied.

Third Criterion of High Risk Score:

According to the invention, the determination of a third criterion of high risk score is at least a function of the evolution of the values of venous pressure, of the evolution of the values of arterial pressure and of the evolution of the effectiveness values determined between an anterior session (i) and a posterior session (j).

More particularly, the determination of the third criterion of high risk score comprises:

the comparison of the evolution of the effectiveness (E(j)−E(i)) in relation to the value of the effectiveness of the anterior session (E(i)), and the comparison of the evolution of the arterial pressure (Pa(j)−Pa(i)) and venous pressure (Pv(j)−Pv(i)) with a predetermined value.

More particularly, the determination of the third criterion of high risk score consists in determining whether:

the absolute value of the variation in the effectiveness (E(j)−E(i)) between the anterior session (i) and the posterior session (j) is greater than or equal to 10%, preferably 20% of the value of the effectiveness of the anterior session (E(i)), and the increase in the venous pressure (Pv(j)−Pv(i)) between the anterior session (i) and the posterior session (j) is greater than or equal to 50 mmHg, and the decrease in the arterial pressure (Pa(j)−Pa(i)) between the anterior session (i) and the posterior session (j) is less than or equal to 50 mmHg, the score being high if these three conditions are satisfied.

Fourth Criterion of High Risk Score:

According to the invention, the determination of a fourth criterion of high risk score is at least a function of the evolution of the values of venous pressure (Pv(j)−Pv(i)), the evolution of the values of arterial pressure (Pa(j)−Pa(i)) and the evolution of the effectiveness values (E(j)−E(i)) determined between an anterior session (i) and a posterior session (j).

More particularly, the determination of the fourth criterion of high risk score comprises the comparison of each of said three parameter evolutions in relation to the value of the parameter of the anterior session.

More particularly, the determination of the fourth criterion of high risk score consists in determining whether:

the increase in the venous pressure (Pv(j)−Pv(i)) between the anterior session (i) and the posterior session (j) is greater than or equal to 10%, preferably 20% of the value of the venous pressure of the anterior session (Pv(i)), and the decrease in the arterial pressure (Pa(j)−Pa(i)) between said sessions is greater than or equal to 10%, preferably 20% of the value of the arterial pressure (Pv(i)) of the anterior session, the score being high if these two conditions are satisfied.

Fifth Criterion of High Risk Score:

According to the invention, the determination of a fifth criterion of high risk score is at least a function of the evolution of the purification effectiveness (E(i)−E(j)) between an anterior session (i) and a posterior session (j).

More particularly, the determination of the fifth criterion of high risk score comprises the comparison of the evolution of the purification effectiveness (E(i)−E(j)) with a predetermined value.

More particularly, the determination of the fifth criterion of satisfied high risk score consists in determining whether the decrease in the purification effectiveness (E(i)−E(j)) between the anterior session (i) and the posterior session (j) is greater than or equal to 40 ml/min, the score being high if this condition is satisfied.

According to the invention:

for the determination of the first criterion of high risk score, if the number of sessions considered is greater than two, the determination can be made for each session considered.

for the determination of the second criterion of high risk score, if the number of sessions considered is greater than two, the determination can be made for at least two successive sessions (i,i+1).

for the determination of at least one from among the third, fourth and fifth criteria of high risk score, if the number of sessions considered is greater than two, the anterior session can be the first temporal session considered and the posterior session can be the last temporal session considered, for the determination of at least one from among the third, fourth and fifth criteria of high risk score, if the number of sessions considered is greater than two, the temporal sessions considered can be those for which the values of at least one parameter considered are the most distant.

Determination of Zero Risk Score (0):

This determination has as result:

a zero score when six criteria of zero risk score are all fulfilled, or a non-zero score when at least one from among the six zero score criteria is not fulfilled.

First Criterion of Zero Risk Score:

According to the invention, the determination of a first criterion of zero risk score is at least a function of the effectiveness parameter and the extracorporeal blood flowrate determined for at least two sessions.

More particularly, the determination of the first criterion of zero risk score is performed by comparing, for at least two sessions, each value of the effectiveness parameter of a session with a linear function of the value of the extracorporeal blood flowrate of the same session.

More particularly, the determination of the first zero risk criterion consists in determining, for at least two sessions, if each value of the determined effectiveness of a session lies on or above the straight line of equation:

$$E(i)=0.4*Qb(i)+40,$$

with Qb(i) being the extracorporeal blood flowrate for the same session (i), the first criterion of zero risk score being satisfied in this case.

Second Criterion of Zero Risk Score:

According to the invention, the determination of a second criterion of zero risk score is at least a function of the values of the venous pressure and the arterial pressure and the values of the blood flowrate of the patient determined for at least two sessions.

More particularly, the determination of the second criterion of zero risk score is made by comparing, for at least two sessions, each value of the arterial pressure (Pa(i), . . . , Pa(j)) with a linear function of the blood flowrate (Qb(i), . . . , Qb(j)) of the session and each value of the venous pressure value (Pv(i), . . . , Pv(j)) with a linear function of the blood flowrate of the session (Qb(i), . . . , Qb(j)).

More particularly, the determination of the second criterion of zero risk score consists in determining for at least two sessions (i, j):

whether each absolute value of the arterial pressure (Pa(i), Pa(j)) determined per session is less than or equal to half the blood flowrate of the patient (Qb(i), ..., Qb(j)) for the session considered (i, j), and whether each value of the venous pressure (Pv(i), ..., Pv(j)) determined per session is less than or equal to half the blood flowrate of the patient (Qb(i), ..., Qb(j)) for the session considered (i, j), the second risk score criterion being considered zero in this case.

Third Criterion of Zero Risk Score:

According to the invention, the determination of a third criterion of zero risk score is at least a function of the evolution of the extracorporeal blood flowrate (Qb(j)–Qb(i)) between an anterior session (i) and a posterior session (j).

More particularly, the determination of the third criterion of zero risk score comprises the comparison of the evolution of the blood flowrate of the patient with a predetermined value.

More particularly, the determination of the third criterion of zero risk score consists in determining whether the absolute value of the variation in the blood flowrate (|Qb(j)–Qb(i)|) between an anterior session (i) and a posterior session (j) is less than or equal to 20 ml/min, the third risk score criterion being considered zero in this case.

Fourth Criterion of Zero Risk Score:

According to the invention, the determination of a fourth criterion of zero risk score is at least a function of the evolution of the values of arterial pressure (Pa(j)–Pa(i)) between an anterior session (i) and a posterior session (j).

More particularly, the determination of the fourth criterion of zero risk score comprises the comparison of the evolution of the arterial pressure (Pa(j)–Pa(i)) with the value of the arterial pressure (Pa(i)) of the anterior session (i).

More particularly, the determination of the fourth criterion of zero risk score consists in determining whether the variation in the arterial pressure (Pa(j)–Pa(i)) between the anterior session (i) and the posterior session (j) is less than or equal to 10%, preferably to 20%, of the arterial pressure (Pa(i)) of the anterior session, the fourth risk score criterion being considered zero in this case.

Fifth Criterion of Zero Risk Score:

According to the invention, the determination of a fifth criterion of zero risk score is at least a function of the evolution of the values of venous pressure (Pv(j)–Pv(i)) between an anterior session (i) and a posterior session (j).

More particularly, the determination of the fifth criterion of zero risk score comprises the comparison of the evolution of the venous pressure (Pv(j)–Pv(i)) with the value of the venous pressure of the anterior session (Pv(i)).

More particularly, the determination of the fifth criterion of zero risk score consists in determining whether the variation in the venous pressure (Pv(j)–Pv(i)) between the anterior session (i) and the posterior session (j) is less than or equal to 10%, preferably to 20%, of the venous pressure (Pv(i)) of the anterior session, the fifth risk score criterion being considered zero in this case.

Sixth Criterion of Zero Risk Score:

According to the invention, the determination of a sixth criterion of zero risk score is at least a function of the evolution of the effectiveness of the treatment ((E(j)–E(i)) between an anterior session (i) and a posterior session (j).

More particularly, the determination of the sixth criterion of zero risk score comprises the comparison of the evolution of the effectiveness of the treatment ((E(j)–E(i)) with a predetermined value.

More particularly, the determination of the sixth criterion of zero risk score consists in determining whether the absolute value of the variation in the effectiveness of the treatment ((E(j)–E(i)) between the anterior session (i) and the posterior session (j) is less than or equal to 10 ml/min, the sixth risk score criterion being considered zero in this case.

In the method for determining the zero risk score:

for the determination of at least one from among the first and the second criteria of zero risk score, if the number of sessions considered is greater than two, the determination is made for each session considered, for the determination of at least one from among the third, fourth, fifth and sixth criteria of zero risk score, if the number of sessions considered is greater than two, the anterior session can be the first temporal session considered and the posterior session can be the last temporal session considered, for the determination of at least one from among the third, fourth, fifth and sixth criteria of zero risk score, if the number of sessions considered is greater than two, the temporal sessions considered can be those for which the values of at least one parameter considered are the most distant.

In the method according to the invention, the treatment sessions considered are spread over at least two weeks, preferably over an interval lying between 2 weeks and 6 months, more preferably over an interval of 3 weeks.

The invention also relates to a method for determining reliability of risk score of the state of a vascular access comprising the following steps:

first implementation of the method for determining the state of a vascular access over a first time interval defined between an anterior session and a posterior session and comprising more than two sessions, taking into account of the first risk score determined, at least one second implementation of the method for determining the state of a vascular access over at least one second time interval situated inside the first determined interval, taking into account of the second risk score determined, calculating the reliability as a function of the first score determined and at least of the second score determined.

More particularly, when a number n of risk scores is determined by n implementations of the method for determining the state of a vascular access, the calculation of a reliability percentage is operated by the ratio of the number of identities between the first risk score determined over the first interval and each of the other risk scores determined over an interval inside the first interval divided by the number n.

More particularly, the second time interval has as posterior bound the posterior session of the first interval.

It should be clearly noted that the method according to the invention is not necessarily implemented during the treatment. Preferably, it is implemented after a treatment session, if the parameters considered are mean parameters over a session.

The invention finally relates to a computer program for determining the state of a vascular access of a patient, which program is loadable into the internal memory of a computer, comprising portions of computer program code for, when the program is executed by the computer, implementing the method for determining the state of the vascular access and/or the method for determining reliability of risk score of the state determined.

This program can be recorded on a readable support in a computer, the support being an optical and/or magnetic data memory or a volatile storage support.

Concerning the invention in general, the risk score takes 3 values according to the information provided by the parameters examined.

The zero risk score corresponds to the patients examined who are stable in a normality zone for a recent and sufficiently long time period.

The intermediate risk score corresponds to the patients examined who may be outside of the normality zone, but who do not have any recent aggravation of their vascular access making it possible to envisage a short-term complication.

The high risk score corresponds to the patients examined exposed to a short-term complication which threatens the functionality of the vascular access.

Advantages of the Determination According to the Invention for Monitoring the Vascular Access:

The invention affords a maximum of advantages of which the main ones are listed here:
- swiftness of the evaluation of a risk of the vascular access,
- implementation of the invention without necessary additional hardware;
- time saving of additional treatment or intervention on the patient;
- saving of additional labor costs, of consumable medical apparatus, of hardware (use of Doppler . . . )
- implementation of the invention without additional manipulation during treatment, and without intervention during dialysis sessions, therefore without producing disturbances,
- alert levels sorted by priority with a high risk score and an intermediate risk score;
- remote monitoring of several patients and/or in one or more clinics,
- remote monitoring of a home dialyzed patient by a physician,
- anticipation of the risky state of the vascular access before the start of a dialysis session,
- ranking according to several levels of significance of the risk of the vascular access,
- the calculated scores can be sent directly to the physician.

In patients with zero score, the invention makes it possible to avoid expensive explorations and/or examinations repeated by regular (each week for example) and systematic analysis.

In patients with intermediate score, a rather more normal situation is detected, but the analysis steers the physician towards complementary examinations and/or steers the physician to prescribe an update of the prescription for the extracorporeal treatment.

In patients with high score, there is a time gain in the indication of invasive exploration, and therefore there are better chances of saving a vascular access and of accessing possibilities of efficacious treatments in regard to extrarenal purification.

The invention claimed is:

1. A calculation and control system for determining whether a patient intended to follow several sessions (i, j) of extracorporeal blood treatment by drawing and return of the blood via the vascular access, falls or not within a group among several groups of hypertension-affected patients, the systems comprising the following means:
 a) means for determining the value of at least one parameter ($\Delta Pi$, $\Delta Pj$ . . . ) representing the evolution of the interdialytic mass ($\Delta P$) of the patient, for at least two sessions (i, j . . . ),
 b) means for determining the value (CPi, CPj, . . . ) of at least one parameter representing the plasmatic conductivity (CP) of the patient for at least two sessions (i, j),
 c) means for determining the value (TMi, TMj) of a parameter representing the ionic mass transfer of the treatment for at least two sessions (i, j),
 d) programmed means for determining whether the patient falls or not within a group of hypertension-affected patients as a function of the evolution over several sessions of at least one of the three following sets of values:
  a first set of at least two determined values ($\Delta Pi$, $\Delta Pj$) of the evolution of the interdialytic mass ($\Delta P$) of the patient,
  a second set of at least two determined values (CPi, CPj . . . ) representing the plasmatic conductivity; and
  a third set of at least two determined values (TMi, TMj) representing the ionic mass transfer.

2. The system according to claim 1, wherein the hypertension groups are divided into a first group of hypertension-affected patients, a second group of hypertension-affected patients and a third group of hypertension-affected patients.

3. The system according to claim 2, wherein the programmed means for determining the belonging to a group of hypertension-affected patients comprise programmed means for determining whether the patient falls within the first group.

4. The system according to claim 3, wherein the programmed means for determining the belonging to a group of hypertension-affected patients comprise programmed means for determining whether the patient falls within the second group when the patient does not fall within the first group.

5. The system according to claim 4, wherein the programmed means for determining the belonging to a group of hypertension-affected patients comprise programmed means for determining whether the patient falls within the third group when the patient does not fall within the second group.

6. The system according to claim 1, wherein the value ($\Delta Pi$, $\Delta Pj$ . . . ) representing the interdialytic evolution of the mass ($\Delta P$) of the patient, for at least two sessions (i, j . . . ) is chosen from the group comprising:
 the weight increase of the patient between the end of one session (i) and the beginning of the following session (i+1)),
 the mass increase of the patient between the end of one session (i) and the beginning of the following session (i+1),
 a parameter proportional to one of the aforesaid parameters.

7. The system according to claim 1, wherein the parameter representing the plasmatic conductivity is the same as or function of at least one of the following parameters:
 the plasmatic conductivity of the patient,
 the predialytic plasmatic conductivity of the patient, i.e. the plasmatic conductivity before the session of extracorporeal blood treatment, or
 a parameter proportional to one of the aforesaid parameters.

8. The system according to claim 1, wherein the parameter representing the ionic mass transfer for at least two sessions (i, j) is the same as or function of at least one of the following parameters:
 the ionic mass transfer during the session,
 the sodium mass transfer during the patient's session,
 a parameter proportional to one of the aforesaid parameters.

9. The system according to claim 8, wherein the patient is initially regarded as hypertension-affected when the values representing his/her pressure increase of at least about 20 mmHg over at least two sessions and/or the value representing his/her pressure for one session is above about 150 mmHg.

10. The system according to claim 9, wherein the programmed means for determining whether the patient falls or not within the first group of hypertension-affected patients are programmed means for determining whether the values representing the evolution of the interdialytic mass of the patient (ΔP) over several sessions (i, j) show a tendency to decrease, the patient being regarded as falling within the first group when the tendency is to decrease.

11. The system according to claim 10, wherein the means for determining the belonging to the first group of hypertension-affected patients will consider the belonging to the first group when the evolution of the values representing the mass is above about one kilogram.

12. The system according to claim 1, comprising means for determining the patient's pressure.

13. The system according to claim 1, wherein the programmed means for determining whether the patient falls within the second group of hypertension-affected patients are programmed means for determining whether the values representing the plasmatic conductivity (CP) over several sessions (i, j) show a tendency to increase or furthermore a tendency to decrease, the patient being considered as falling within the second group when the tendency is to increase or furthermore to slightly decrease.

14. The system according to claim 13, wherein the means for determining whether the patient belongs to the second group of hypertension-affected patients will consider the belonging to the second group when the values representing the plasmatic conductivity increase or decrease of less than about 0.3 mS/cm.

15. The system according to claim 1, wherein the programmed means for determining the non-belonging to the second group of hypertension-affected patients are programmed means for determining whether the values representing the plasmatic conductivity (CP) over several sessions (i, j) show a tendency to decrease.

16. The system according to claim 15, wherein the programmed means for determining the non-belonging to the second group of hypertension-affected patients will consider the non-belonging to the second group when the values representing the plasmatic conductivity decrease of at least about 0.3 mS/cm.

17. The system according to claim 1, wherein the programmed means for determining the belonging to the third group of hypertension-affected patients are programmed means for determining whether the values representing the ionic mass transfer (TM) over several sessions (i, j) shows a tendency to decrease, the third level being regarded as fulfilled when the tendency is to decrease.

18. The system according to claim 17, wherein the means for determining the belonging to the third group of hypertension-affected patients will consider the belonging to the third group when the values representing the plasmatic conductivity decrease of at least about 200 mmol/session.

19. The system according to claim 1, wherein for the determination of the belonging to one of the three groups of hypertension-affected patients, if the number of sessions taken into account is above two, the corresponding means of determination are intended to operate with at least two successive sessions (i, i+1).

20. The system according to claim 1, wherein for the determination of the belonging to one of the three groups of hypertension-affected patients, if the number of sessions taken into account is above two, the corresponding means of determination are intended to operate by identifying the first temporal session considered as anterior session and by identifying the last temporal session considered as posterior session.

21. The system according to claim 1, wherein for the determination of the belonging to one of the three groups of hypertension-affected patients, if the number of sessions taken into account is above two, the corresponding means of determination are intended to regard as temporal sessions those for which the values of at least one parameter taken into account are the most distant.

22. The system according to claim 1, comprising programmed means for urging or monitoring the change of at least one medical parameter or of at least one machine parameter for each group of hypertension-affected patients.

23. The system according to claim 22, comprising programmed means for, when the belonging to the first group of hypertension-affected patients is taken into account, suggesting or monitoring during a future session the decrease in the patient's mass or weight to be reached at the end of the session.

24. The system according to claim 23, comprising programmed means for, when the belonging to the second group of hypertension-affected patients is taken into account, suggesting the decrease in the amount of salt taken by the patient from one session to the other.

25. The system according to claim 22, comprising programmed means for, when the belonging to third group of hypertension-affected patients is taken into account, suggesting or monitoring during a future session the decrease in the value representing the dialytic conductivity.

26. The system according to claim 25, wherein the suggested or monitored decrease in dialytic conductivity is of at least about 0.2 mmol.

27. The system according to claim 1, wherein the programmed means for suggesting or monitoring said decrease in the patient's mass are controlled so that the decrease in the value representing the mass is of at least about 0.5 kg, or about 1 kg.

28. The system according to claim 1, wherein the treatment sessions taken into account are spread over several sessions over a time lapse of about six months, preferably about 3 months.

29. A computer comprising:
   storage means storing at least values of at least one parameter (Pi, Pj ... ) representing the mass (P) of the patient, at least values of at least one parameter (CPi, CPj ... ) representing the patient's plasmatic conductivity, and values of at least one parameter representing the ionic mass transfer (TMi, TMj ... ) relating to at least one patient undergoing several sessions (i, ... j) of extracorporeal blood treatment,
   a calculation and control system according to claim 1, for determining whether the patient whose parametric values of at least one parameter (Pi, Pj ... ) representing the mass (P) of the patient, whose values of at least one parameter representing the plasmatic conductivity (CP) and whose values of at least one parameter representing the ionic mass transfer are stored in said storage means, falls or not within a group of hypertension-affected patients.

30. A computer according to claim 29 further comprising:
   storage means storing at least values of at least one extracorporeal hemodynamic parameter (P1i, ... P1j, ... P2i, ... P2j ... ) and purification effectiveness values (E(i), ... E(j)) relating to at least one patient subjected to several sessions (i, ... j) of extracorporeal blood treatment,
   a calculation and control system according to claim 1 for the determination of the vascular state of the patient the parametric values of at least one of whose extracorporeal hemodynamic parameters (P1i, ... P1j, ... P2i, ...

P2*j* . . . ) and whose purification effectiveness values (E(i), . . . E(j)) are stored in said storage means.

31. An extracorporeal blood treatment machine comprising at least:
    a blood treatment unit capable of implementing an extracorporeal blood treatment by blood circulation via an extracorporeal blood circuit comprising an arterial line, a first chamber of a filter separated by a semi-permeable membrane, a venous line, and by dialysate circulation in a second chamber of the filter,
    storage means storing at least values of at least one parameter (Pi, Pj . . . ) representing the mass (P) of the patient, at least values of at least one parameter (CPi, CPj . . . ) representing the patient's plasmatic conductivity, and values of at least one parameter representing the ionic mass transfer (TMi, TMj . . . ) relating to at least one patient undergoing several sessions (i, . . . j) of extracorporeal blood treatment,
    a calculation and control system according to claim 1 for determining whether the patient whose parametric values of at least one parameter (Pi, Pj . . . ) representing the mass (P) of the patient, whose values of at least one parameter (CPi, CPj . . . ) representing the patient's plasmatic conductivity and whose values of at least one parameter representing the ionic mass transfer (TMi, TMj . . . ) are stored in said storage means, falls or not within a group of hypertension-affected patients.

32. A network comprising:
    a server,
    at least one blood treatment machine linked to the server, each machine comprising:
        means for measuring and/or for calculating medical data relating at least one parameter (Pi, Pj . . . ) representing the mass of the patient, at least one parameter (CPi, CPj . . . ) representing the patient's plasmatic conductivity and at least one parameter representing the ionic mass transfer (TMi, TMj . . . ),
        means for sending at least part of these measured and/or calculated data to the server,
    the server comprising:
        means for receiving at least part of the medical data relating to extracorporeal blood treatments,
        storage means for storing the data received from the reception means from one or more blood treatment machines,
        a calculation and control system according to claim 1, intended to operate on the basis of said received data,
    at least one station capable of communicating with the server for receiving at least the results of the implementation of said calculation and control system.

33. The network according to claim 32, wherein said station comprises a unit for displaying the results relating to the determined group of hypertensions-affected patients.

34. A calculation and control system according to claim 1, also for the determination of the state of a vascular access of a patient intended to follow successive sessions (i, j) of extracorporeal blood treatment by drawing and return of the blood via the vascular access, the system comprising the following means:
    a) means for determining the value (P1*i*, P1*j*, P2*i*, P2*j*, . . . ) of at least one hemodynamic extracorporeal parameter (P1, P2 . . . ) of the patient for at least two sessions (i,j),
    b) means for determining the value (Ei, Ej) of the purification effectiveness of the treatment for at least two sessions (i, j),
    c) programmed means for determining a risk score relating to the state of the vascular access of the patient as a function of said at least two values (Pi, Pj) of the hemodynamic extracorporeal parameter and of said at least two determined values (Ei, Ej) of the purification effectiveness.

35. A calculation and control system for determining reliability of risk score of the state of a vascular access comprising means as follows:
    the system according to claim 34,
    means for storing:
        I. a first risk score (S) determined over a first time interval defined between an anterior session and a posterior session and comprising more than two sessions,
        II. at least one second risk score (S') determined over at least one second time interval situated inside the first determined interval,
    programmed means for calculating the reliability as a function of the first score determined and at least of the second score determined (S, S').

36. An extracorporeal blood treatment machine comprising at least:
    a blood treatment unit capable of implementing an extracorporeal blood treatment by blood circulation via an extracorporeal blood circuit comprising an arterial line, a first chamber of a filter separated by a semi-permeable membrane, a venous line, and by dialysate circulation in a second chamber of the filter,
    storage means storing at least values of at least one extracorporeal hemodynamic parameter and purification effectiveness values relating to at least one patient subjected to several sessions of extracorporeal blood treatment,
    a calculation and control system according to claim 34 for the determination of the vascular state of the patient the parametric values of at least one of whose extracorporeal hemodynamic parameters (P1*i*, . . . P1*j*, . . . P2*i*, . . . P2*j* . . . ) and whose purification effectiveness values (E(i), . . . E(j)) are stored in said storage means.

37. A network comprising:
    a server,
    at least one blood treatment machine linked to the server, each machine comprising:
        means for measuring and/or for calculating medical data relating to at least one extracorporeal hemodynamic parameter (P1*i*, . . . P1*j*, . . . P2*i*, . . . P2*j* . . . ) and to the purification effectiveness of the treatment (E(i), . . . E(j)),
        means for measuring and/or calculating medical data relating to at least one parameter (Pi, Pj . . . ) representing the mass of the patient, at least one parameter (CPi, Cpj . . . ) representing the plasmatic conductivity of the patient, and at least one parameter representing the ionic mass transfer (TMi, TMj . . . ),
        means for sending at least part of these measured and/or calculated data to the server,
    the server comprising:
        means for receiving at least part of the medical data relating to extracorporeal blood treatments,
        storage means for storing the data received by the reception means from one or more blood treatment machines,
        a calculation and control system according to claim 34, intended to operate on the basis of said received data,
    at least one station capable of communicating with the server for receiving at least the results of the implementation of said calculation and control system.

38. A method for determining the state of belonging to a group of hypertension-affected patients of a patient intended to follow successive sessions (i, j) of extracorporeal blood treatment by blood extraction and return, the method of determination comprising the following steps:
 a) flowing blood through an extracorporeal machine wherein the machine performs the following steps,
 b) determining the value of at least one parameter (Pi, Pj . . . ) representing the mass (P) of the patient for at least two sessions (i, j . . . ),
 c) determining the value (CPi, CPj, . . . ) of at least one parameter representing the patint's plasmatic conductivity (CP) for at least two sessions (i, j),
 d) determining the value (TMi, TMj) of at least one parameter representing the ionic mass transfer of the treatment for at least two sessions (i, j),
 e) determining whether the patient falls or not within a group of hypertension-affected patients as a function of the evolution over several sessions of at least one of the three following sets of values:
  a first set of at least two determined values (Pi, Pj) representing the evolution of the interdialytic mass of the patient,
  a second set of at least two determined values (CPi, CPj . . . ) representing the plasmatic conductivity; and
  a third set of at least two determined values (TMi, TMj) representing the ionic mass transfer.

39. A computer-readable medium comprising code configured to determine whether a patient falls or not within a group of hypertension-affected patients, implementing the method according to claim 38.

* * * * *